(12) United States Patent
Kerr et al.

(10) Patent No.: US 9,801,539 B2
(45) Date of Patent: Oct. 31, 2017

(54) OCULAR VIDEOGRAPHY SYSTEM

(71) Applicant: Stiftung Caesar—Center of Advanced European Studies and Research, Bonn (DE)

(72) Inventors: Jason Kerr, Tuebingen (DE); Damian Haydon Wallace, Tuebingen (DE); Juergen Sawinski, Reicheneck (DE); David Greenberg, Bloomington, IN (US)

(73) Assignee: STIFTUNG CAESAR—CENTER OF ADVANCED EUROPEAN STUDIES AND RESEARCH, Bonn (DE)

( * ) Notice: Subject to any disclaimer, the term of this patent is extended or adjusted under 35 U.S.C. 154(b) by 427 days.

(21) Appl. No.: 14/286,897

(22) Filed: May 23, 2014

(65) Prior Publication Data
US 2015/0077543 A1 Mar. 19, 2015

Related U.S. Application Data

(60) Provisional application No. 61/826,639, filed on May 23, 2013.

(30) Foreign Application Priority Data
May 23, 2013 (EP) .................................... 13168890

(51) Int. Cl.
H04N 5/33 (2006.01)
A61B 3/113 (2006.01)
(Continued)

(52) U.S. Cl.
CPC .............. *A61B 3/113* (2013.01); *A61B 3/145* (2013.01); *H04N 5/2252* (2013.01);
(Continued)

(58) Field of Classification Search
CPC ........ A61B 2503/40; A61B 1/24; A61B 3/113; A61B 3/145; H04N 5/2252; H04N 5/2256; H04N 5/33; G06K 9/00362
See application file for complete search history.

(56) References Cited

U.S. PATENT DOCUMENTS 5,481,622 A * 1/1996 Gerhardt ................ A61B 3/113
345/158
6,578,962 B1 * 6/2003 Amir .................... G06K 9/0061
345/157

(Continued)

OTHER PUBLICATIONS

European Search Report with Written Opinion, dated Oct. 31, 2014, corresponding to European Patent Application No. 14169665, a related application, 9 pgs.

(Continued)

*Primary Examiner* — Md Haque
(74) *Attorney, Agent, or Firm* — Lathrop & Gage LLP

(57) ABSTRACT

The present invention relates to an Ocular Videography System for tracking eye movements of an animal, in particular rats, comprising a camera system suitable of being positioned on the head of an animal to track eye movements of at least one eye of the animal, a head mount on which the camera system is fixed or fixable, wherein, at least one image sensor as well as at least one decoder, for decoding a signal detected by the image sensor, each being comprised by the camera system, and wherein the camera system, and in particular a camera of the camera system, is designed in such a way that it detects a movement of the eye and/or a movement of the head of the animal in a vertical and/or horizontal and/or a torsional direction to an optical axis of the camera system and/or of the optical axis of the animal's eye without interfering with the animal's natural motion dynamics.

20 Claims, 22 Drawing Sheets

(51) Int. Cl.
  *H04N 5/225*  (2006.01)
  *A61B 3/14*  (2006.01)
(52) U.S. Cl.
  CPC .............. *H04N 5/2256* (2013.01); *H04N 5/33* (2013.01); *A61B 2503/40* (2013.01)

(56) References Cited

U.S. PATENT DOCUMENTS

| | | | |
|---|---|---|---|
| 6,727,940 B1 * | 4/2004 | Oka | ..................... H04N 5/2259 348/211.3 |
| 2002/0003571 A1 * | 1/2002 | Schofield | ................ B60C 23/00 348/148 |
| 2006/0217816 A1 | 9/2006 | Pesaran et al. | |
| 2006/0291363 A1 * | 12/2006 | Noguchi | ............ G02B 27/4238 369/112.08 |

OTHER PUBLICATIONS

European Examination Report, dated Feb. 21, 2017, in European patent application serial No. 14169665.8, 6 pp.

Wallace et al. (2013) "Rats Maintain an Overhead Binocular Field at the Expense of Constant Fusion," Nature 498:65-69, w supplementary information, 55 pp.

* cited by examiner

OCULAR VIDEOGRAPHY SYSTEM

CROSS-REFERENCES TO RELATED APPLICATIONS

This application claims the benefit of priority from U.S. Provisional Application No. 61/826,639, filed on May 23, 2013, and European Patent Application No. 13 168 890.5, filed on May 23, 2013, all of which are incorporated herein by reference in their entirety.

SUMMARY OF THE INVENTION

The present invention relates to an ocular videography system and electronics for tracking eye movements of animals, in particular of rodents, for example rats or the like. Further, the invention relates to an overhead position tracking hardware for automatic detection of the position of the animal in addition to the movement of at least one eye of the animal as well as (software) analysis methods concerning an implementation of said automatic detection of the movement of at least one eye of the animal for example in or related with said ocular videography system.

Studying vision in rodents is one of the cornerstones in mammalian brain research and our research group investigates models of vision in rats. For decades it has been recognized that studying vision ideally would be achieved in the freely moving animal, where the animal is free to interact with its environment. Up until now almost all research into vision has been performed on either head-restrained or anesthetized animals. The problem is how to record accurate eye movements from fully unrestrained animals that have a very limited capacity to carry weight. To obtain accurate eye positions requires not only stable images and a light-weight system but also high frame rates. Central to the present invention is the goal of measuring eye movements in freely moving animals and a development of high accuracy tracking of the pointing direction of the eyes in freely moving animals (to allow us to observe what the animals are looking at) and high accuracy head-position tracking in 3-dimensions (to allow determination of the pose and position of the head for determining the animal's visual targets). The most accurate and non-invasive method for tracking eye positions in humans is oculo-videography (involving acquiring high-speed movies of the pupil of the eyes at high zoom and image resolution, then tracking the position of the pupils in the resulting images). Due to their small size relative to available oculo-videography systems, oculo-videography has not been performed in freely moving rodents. What is proposed in the current invention is a system for determining the direction in which the eyes are pointing with high precision.

Therefore it is an objective of the present invention to establish a recording technique that can accurately record eye movements in all planes of motion of the eye and eye pointing direction relative to the animal while satisfying the following constraints:
  Can be used with rodents, specifically young rats
  Allows full, free movement of the head and body during natural behavior
  Does not interfere with vision or occlude the subject's field of view
  Detects eye rotation on all axes: horizontal, vertical and torsional (twist around optic axis)

In order to solve the present objective, the present invention makes, inter alia, use of a (high-speed) camera system suitable for mounting on the head of an animal, in particular a rodent. In particular the present invention uses, inter alia, a physical separation of an image sensor and a decoder, so that only a minimal number of components are required on the camera carried by the subject.

Therefore, the present invention is based on an Ocular Videography System for tracking eye movements of an animal, in particular rats, comprising a camera system and in particular a camera of the camera system suitable for being positioned on the head of an animal to track eye movements of at least one eye of the animal and a head mount on which the camera system is fixed or fixable. Further, the Ocular Videography System comprises at least one image sensor as well as at least one decoder, for decoding a signal detected by the image sensor, each being comprised by the camera system, and in particular by said camera, wherein the camera system, in particular the camera of said camera system, is designed in such a way that it detects movements of the eye and/or a movement of a head of the animal in a vertical and/or horizontal and/or a torsional direction to an optical axis of the camera system and/or of the optical axis of the animal's eye without interfering with the animal's natural motion dynamics.

Thereby, "horizontal direction" denotes movement of the eye in the anatomical nasal-temporal plane, "vertical direction" denotes movement of the eye in the anatomical dorsal-ventral plane, and "torsional direction" being a direction where each observed feature runs at a predefined distance around the optical axis of the eye along a circular track with its center being the optical axis of the eye.

Electronic communication for control of the camera and transfer of data from the camera is accomplished via lightweight cables light enough for the animal to carry but still suitable for transmitting the required data. In particular the following features could be implemented in said ocular videography system separately or in a predetermined combination with each other:

Data stream for transferring images: conventional twisted-pair connection (using 50 μm enameled copper wire) using low voltage differential signaling (LVDS) directly supported by the image sensor.
  $I^2C$ compatible serial communication for controlling camera function. The sensitivity to voltage levels inherent in this form of data transfer means that thin cables are not suitable, especially in the ground connection (as described in $I^2C$ bus manuals, compare with 'long distance communication'). This problem is ad-dressed either by using a single low-resistance (thicker) ground wire or by galvanically separating camera supply and decoder board ground cables.
  A simple plano-convex lens in reverse orientation including an aperture provides high contrast and large depth of field. This allows detection of fine structure along the boundary of the pupil and thereby torsional rotation of the eye, that being a rotation of the eye around its optical axis.
  The image plane is illuminated off-axis (to reduce reflections on the eyeball) with infrared (IR) light. The light path from illumination to eye to camera includes a reflector that transmits visible light while reflecting IR. This allows the camera to be positioned outside the subject's field of view. The camera is equipped with an IR-transmission filter to prevents light sources in the visible range from interfering with eye tracking.
  Design, manufacture and assembly of a suitable (small and light) mounting arm system for flexible adjustment of the camera's field of view.

Use of time-varying IR illumination for synchronization of eye tracking to other experimental measurements. This approach avoids additional cabling for a frame synchronization signal and allows timing information to be computed from image data alone.

A brief account of the major points of the methodology is presented in the following paragraphs, with detailed accounts of all aspects of the hardware and analysis methods used presented in the following sections.

According to at least one embodiment of the Ocular Videography System the camera system is designed and mounted securely on the head mount without interfering with the animal's field of view. Thereby, a motion of the head can be easily monitored without the animal itself being influenced by said camera system.

According to at least one embodiment of the Ocular Videography System the decoder for decoding the signal detected by the image sensor is mounted off of the animal. This leads so a very lightweight system which can easily be carried from even very small animals as the decoder is mounted apart and at a distance from the animal. In other words, the animal does not have to carry the decoder around.

According to at least one embodiment of the Ocular Videography System the camera system comprises at least one light emitting element for guiding and emitting light towards the animal's eye, at least one light reflector for reflecting at least partially the light reflected from the animal's eye to the image sensor of the camera system, wherein the camera system is mounted on the head mount outside of a visual field of the animal's eye. Mounting the camera system, in particular a camera itself, outside said visual field prevents the animal from seeing any camera so that the animal is not confused by the head mount and/or a camera or anything else of the camera system.

According to at least one embodiment the light emitting element is arranged within the camera system such that it illuminates the animal's eye off-axis to the optical axis of the animal's eye. "Off-axis", thereby means, a direction and/or positioning outside and besides the optical axis. Mounting off-axis said light emitting element automatically can generate an angle between a main radiation direction of the light emitting element and said optical axis, so that light reflected by the animal's eye is being deflected at the same angle back in a direction away from the animal's eye thereby minimizing interference with the detection of the position of the pupil.

According to at least one embodiment of the Ocular Videography System the light emitting element is a light emitting diode (LED) emitting light at least in the infrared optical spectrum. For example, the light emitting diode emits light mainly in a range of the electromagnetic spectrum not visible to the subject.

According to at least one embodiment of the Ocular Videography System the reflector transmits at least partially light in the visible spectrum and reflects light in the infrared spectrum of light. This guarantees that light in the visible spectrum is not impaired by the oculo-videography system and, therefore, the subjects' field of view is minimally obstructed.

According to at least one embodiment of the Ocular Videography System a IR-transmission filter is an element of the camera system, and in particular of the camera of the camera system, wherein said IR-transmission filter is being arranged in an optical path of the light emitted by the light emitting element and prevents the superimposition of light in the visible optical spectrum with light emitted by the light emitting element.

According to at least one embodiment of the Ocular Videography System, said system comprises a head position tracking system designed to track a position of the animal's head within a predefined, stationary coordinate system originating outside the animals body, wherein said head position tracking system comprises three tracking arms mounted on the head mount in a predefined position to each other, wherein on each of the tracking arms one or more light emitting elements, in particular light emitting diodes (LEDs), being different to the light emitting element for guiding light in the animal's eye, are mounted, and the head position tracking system further comprises a head movement detection device mounted off of the animal's body and stationary within the coordinate system, wherein the head movement detection device detects a movement of the light emitting elements and is designed to calculate a position of the animal's head, within said stationary coordinate system, according to the position and/or the movement of the light emitting elements.

According to at least one embodiment of the Ocular Videography System the camera system comprises a lens unit for guiding light at least partially emitted by the camera system's light emitting element into the image sensor of the camera system.

According to at least one embodiment of the Ocular Videography System the plano-convex lens comprises an aperture of at least 0.02 mm to at most 1.2 mm, preferably at least 0.3 mm to at most 0.5 mm.

According to at least one embodiment of the Ocular Videography System the lens unit is glued to the camera chip.

According to at least one embodiment of the Ocular Videography System a core engine implemented within a processor of the camera system is controlling measurement parameters of the camera system and is capable of streaming data onto one or several hard drives.

According to at least one embodiment of the Ocular Videography System the core engine is capable of processing independent eye movements of both eyes of the animal.

To record eye movements in freely moving rats the applicant developed a miniaturized ocular-videography system that consisted of at least two lightweight head-mounted cameras (FIG. 1). Each camera weighed ~0.8 g and could record continuously at 40-50 Hz at full resolution (752 by 480 pix). Illumination, not visible to rats 1-3, was provided by infrared light-emitting diodes (IR-LEDs, 850 nm) and a small hot-mirror (reflecting infrared but transparent to visible light) allowed the cameras to be positioned in a way that minimized disturbance to the animal's visual field (FIG. 1). Full details of the camera system are given in the section "Miniaturized ocular videography system" below, while details of animal handling and preparation for mounting of the camera system are given in the section "Animals and surgery."

Recordings were made while the animals were performing a gap-crossing task on a raised linear track. The track was divided in half, one end being movable for varying the distance of the gap. Stimulus monitors were located at the ends of the track, and a water spout positioned at the base of each monitor to provide water rewards as an appetitive stimulus. The entire track was surrounded by thick, black felt fabric.

Pupil positions within each acquired video frame were tracked using custom written algorithms (see "Eye tracking method"). To ensure stable tracking of the pupil and to measure camera stability, we also tracked multiple anatomical features of the eyes (tear duct on the medial side and junctions of the eye lids (lateral canthus) on the lateral side) within the images. By tracking these anatomical features we could eliminate the vast majority of movement due to camera motion (FIG. 14). Errors associated with the tracking algorithms were minimal. Pupil and corner positions could be manually marked in each image, but we also developed an automated eye tracking method to facilitate this process. In the automated method, the pupil was identified in each image by detecting circular or elliptical dark-to-light transitions in the image. This was done by analysis of vertical and horizontal brightness gradients in the image (see "Calculation of gradients in eye images" in the "Eye tracking method" subsection of "Analysis methods"). The eye corners were automatically detected using a template-matching approach (see "Compensation for lateral eyeball displacement" in the "Eye tracking method" subsection of "Analysis methods"). Eye orientation was then determined by analyzing the shape of the pupil in the image. When the optical axis of the eye points directly into the camera the pupil appears circular. However, as the eye rotates and the pupil moves towards the edge of the eyeball in the image, the pupil appears progressively more elliptical. The orientation of the eye in a given image was therefore determined by comparing the shape of the pupil in the image to pupil shapes computed for rotations of a realistic 3-dimensional model of the eye (see "Eye tracking" in subsection "Eye tracking method" of "Analysis methods"). Whenever used, automatically-detected pupil and corner positions were manually verified, and were crossed-checked by a second experimenter before being accepted for inclusion in the dataset for further analysis.

The accuracy of the pupil detection algorithm was measured to be <1° (see "Estimation of error in pupil detection method") and given that the standard deviation of the tracked anatomical features, including deviations due to actual movements of the eye, never exceeded 10 pixels, errors from this source are estimated to be <<3°. Pupil positions are presented as degrees of deflection from an origin arbitrarily chosen to lie on the equatorial circumference of the eyeball at the geometric midpoint between the two corners of the eye (see coordinate axes in FIG. 15a).

To allow analyses of the observed eye movements in the context of the rat's pose and location on the track, we also tracked the position and orientation (pitch, roll and yaw) of the animal's head using a custom-built tracking system. Six IR-LEDs were mounted on the head of the animal with the ocular-videography system (FIG. 1), and imaged with four high-speed digital cameras. Head position and orientation were then calculated from the relative position of the LEDs. Tracking was done using custom-written software, and as for eye tracking, LED positions in single images could be either manually marked or automatically detected. Details of the equipment used for position tracking are given below in the section entitled "Overhead position tracking hardware", while details of the software used for automated detection of the tracking LEDs are given in the subsection "Head tracking" in "Analysis methods". Tracking accuracy was <1° for all three axes of head orientation. All the analysis approaches briefly described above require mapping of 3D objects accurately onto the acquired images, and this was done here using a camera model for each of the cameras used. Full descriptions of the mathematics and implementation of these models are described in the section "Analysis methods" below Details of the procedures for animal handling and for preparation and mounting of the camera system are given in the section "Animals and surgery", while details of the behavioral experiments are given in the "Behavioral experiments" section.

Analysis Methods

Animals and Surgery

All surgical and experimental procedures were approved by the local authorities (Regierungspraesidium, Tübingen, Referat 35, Veterinärwesen). Experimental animals for video oculography experiments were male Lister Hooded rats obtained from Charles River Laboratories, Germany. Animals were all maintained on a reversed 12 hour light-dark cycle throughout all procedures, including initial surgery for headplate implantation, training and data recording. All recordings were carried out in the afternoon, typically between 3 and 7 pm, and the animals were between 6 and 9 weeks of age at the time the datasets were acquired. Animals were first implanted with a custom designed titanium headplate which was used for restraining the position of the animal's head during positioning of the system for video oculography (described below). Headplate implantation followed a modified version of the procedure described in. In brief, animals were anaesthetized with a ketamine and xylacine solution (100 mg/kg and 5 mg/kg respectively) and body temperature was maintained at 37° C. using a heating pad and thermal probe. The skin and connective tissue overlying the dorsal aspect of the parietal and interparietal bones was removed and the bone cleaned. The headplate was then centered over a point on the sagittal suture ~3.5 mm posterior to bregma, oriented to be as close as possible to parallel to the dorsal surface of the parietal bone, and fixed in position using light-curing dental adhesive (Optibond FL, Kerr Corp., Orange, Calif., USA), light-curing dental composite (Charisma, Heraeus Kulzer, Hanau, Germany) and dental cement (Paladur, Heraeus Kulzer, Hanau, Germany). The margins of the skin incision were closed using cyanoacrylate adhesive (Histoacryl, B. Braun, Melsungen, Germany), and the animals administered flunixin-meglumin (2 mg/kg) for post-operative analgesia.

After recovery from surgery, animals were habituated to head fixation as follows. Animals were first made accustomed to handling by the experimenters in brief (5-10 min) sessions, prior to initial habituation to head fixation, which was achieved by brief sessions (1 min) in which the headplate was manually held in a fixed position by the experimenter. Following 2-3 such sessions, animals were habituated to head restraint in a custom-made holder in which animals were restrained for progressively increasing durations during daily sessions.

For recording sessions, animals were first head restrained and the oculography system was attached to the headplate. The two cameras were placed for optimal imaging of the left and right eyes, and then fixed rigidly in place. The animal was then released from restraint and placed on either a raised U-shaped track (track width 8 cm, short side segment lengths 60 cm, long central segment length 102 cm, raised 105 cm from the ground, with a 1 cm rim around all edges of the track), or a linear track composed of two platforms (each platform 50 cm long and 26 cm wide, with a 5 cm high rim around the three edges not facing the other platform, raised 107 cm from the ground) one of which could move horizontally to introduce a gap between the platforms (based on gap-crossing apparatus described previously[5,6]). To increase the extent to which the animals explored the tracks during recording sessions, animals were water restricted in the days prior to the sessions (restriction to a daily consumption of no more than 30% of the ad libitum daily water consumption) and the track equipped with two computer controlled water ports which delivered 20 µl boluses of water under the timing control of the experimenter. Under this protocol, animals quickly learned to run from one port to the other in succession to collect water.

Behavioral Experiments

Four male Lister-hooded rats between approx. 5 and 7 weeks of age at the time of the experiments were used in this part of the study. Animals were placed in an open field arena made of transparent Perspex and measuring 80×40×30 cm (length×width×height). The open field contained a single cork log cut in half (approx. 20 cm long and 10 cm wide, arching to a max. height of ~8 cm) to form a semi-circular shelter under which the rat could explore or retreat to seek shelter. The floor of the arena was covered with standard cage bedding (woodchips). The arena was surrounded on three sides by stimulus monitors and an additional stimulus was located directly above the arena. The viewable areas for the monitors were 58×32 cm for the monitors against the short sides of the arena, 81×41 cm for the monitor on the long side of the arena and 71×39 cm for the monitor above the arena. One of the long sides of the arena was left without a monitor for access purposes. All monitors were adjusted to have the same luminance for white. Animals were initially released into the arena with all stimulus monitors displaying a black full-field stimulus, with the room in which the experiments were conducted otherwise dark. After several minutes for the animal to acclimatize and explore the arena, the stimulus on all monitors was changed to a white, full-field stimulus. The switch from black to white full-field stimulus did not elicit any obvious behavioral responses from any of the animals tested. After another period of 1 to 3 minutes, a moving stimulus (either a spot of 15° radius moving approx. 30°/s, or a bar of 10×40° moving 30°/s) was displayed on one of the monitors beside the arena. Stimulus onsets were all initiated manually, and wherever possible, the onset was timed so that the stimulus began when the animal was in the open (not under the log). After both the spot and bar stimulus had been presented once each on each of the three monitors beside the arena, one of the two stimuli chosen at random was presented on the monitor above the arena. After the animal had resumed exploratory behavior the other moving stimulus was presented on the overhead monitor. Stimulus sizes and velocities were matched on all monitors. Behavioral responses were recorded using a digital camera (piA640-210 gm; Basler AG, Ahrensburg, Germany) at 50 Hz frame rate. For synchronization, the frame exposure signal from the digital camera was recorded using a Power 1401 digitizer (Cambridge Electronic Design, Cambridge, UK), and the onset and offset of visual stimuli recorded using a small timing signal presented in the corner of the stimulus monitors, detected using a light-sensitive diode circuit and recorded on the digitizer with the camera frame exposure signal. The timing signal and light-sensitive diode were covered with black tape and therefore not visible to the animal.

The behavioral responses of the animals were analyzed manually by frame by frame inspection of the video files. Underneath the log was defined as the first frame in which the base of the animal's tail emerged from or disappeared under the log, with the "time to next shelter" duration defined as the time between the onset of the stimulus reported by the light-sensitive diode signal and the next time the animal was under the log as defined above. The "Frac. time under shelter" duration was defined as the fraction of the 100 s following the stimulus onset that the animal spent underneath the shelter. The "no stimulus" control times were taken from data recorded prior to display of the first stimulus of any kind. The random time control data were obtained by randomly selecting "hypothetical stimulus" times through the datasets, and then quantifying the time from these random times to the next visit underneath the shelter and the fraction of the 100 s following these times that the animal was underneath the shelter. Statistical comparisons were done with a non-parametric Kruskal-Wallis test followed by a multiple comparison test across all groups (Side stimulus, overhead stimulus, "No stim." and "Random time control") with Bonferroni adjustment. The alpha level for these tests was set to 0.01. Analyses were performed in Matlab.

Miniaturized Ocular Videography System

The eye cameras used for ocular videography were built around a standard 1/3" CMOS image sensor (Aptina Imaging, MT9V024, Framos Imaging Solutions GmbH, Pullach, Germany). The monochrome version of this sensor has a frame rate of 60 Hz at full resolution (752×480 pixels) using a global shutter and a broad wavelength range extended into the near infrared (10% quantum efficiency at about 970 nm). The sensor was controlled with a two-wire serial interface (compatible to NXP's I2C bus), and image data was transmitted serially using low-voltage differential signalling (LVDS).

The camera chip was mounted on a custom-designed printed (PCB) and flexible circuit board (FPC) combination. The FPC carried a standard I2C bus repeater soldered to a 2 m custom harness consisting of cables for power supply, two-wire serial control and a twisted pair for LVDS transmission. The LVDS signal was decoded using a 12-bit deserializer, and fed into a decoder board (Aptina Imaging, Demo2X Board, Framos Imaging Solutions GmbH, Pullach, Germany) which was connected to an acquisition computer via USB. Images were acquired using custom-built software in Matlab and C++ using the Aptina Midlib API, and saved without compression.

The camera optics consisted of a plano-convex lens (focal length 6 mm, Ø3 mm, BK7 glass, Pörschke GmbH, Höchst im Odenwald, Germany) and an IR filter (Optics Balzers, Calflex KS93/45, Qioptiq, Luxembourg). The eye was illuminated using an infrared-light emitting diode (IR-LED, $\lambda$=850 nm, Osram SFH4050, RS-Components, Mörfelden-Walldorf, Germany), and disturbance to the animal's field of vision minimized using an IR-reflector (Optics Balzers, Calflex X, Qioptiq, Luxembourg), transparent in the visible wavelength range.

Each camera weighed about 0.8 g when fully assembled and was mounted via a mounting arm onto a light-weight (approx. 0.5 g) custom-designed plastic housing which could be attached to the titanium headplate implanted on the animal's head. The mounting arm was approximately 1 cm long, and was attached to the housing via a ball joint to allow the camera to be positioned accurately for acquiring images of the animal's eyes.

Overhead Position Tracking Hardware

The animal's head position and orientation were tracked by recording the motion of six IR-LEDs ($\lambda$=850 nm, Osram SFH4050, RS-Components, Mörfelden-Walldorf, Germany) mounted on three plastic struts attached to the oculography system and extending forward, backwards-left and backwards-right. Three-dimensional positions of the six position tracking IR-LEDs were measured using a micrometer, and described in an "LED coordinate system" where the frontmost LED was located at the origin, the outer LEDs on each strut defined the plane z=0, and the inner LED on the front strut was located in the plane y=0. Infrared videography of the position-tracking LEDs was performed at 100 or 150 Hz using 4 CCD cameras (piA640-210 gm; Basler AG, Ahrensburg, Germany) equipped with C-mount 8 mm focal length objectives (M0814MP, Computar, Commack, N.Y., USA). The 4 cameras were mounted ~2 meters above the track or jump-task platforms, such that the LEDs were always in view of at least two cameras. CCD gain was set to the minimum possible value to reduce noise, while LED power and camera exposure times were adjusted to make the position-tracking LEDs significantly brighter than any other image features, while minimizing exposure times to prevent blurring. Typically, exposure times were set to ~0.5 ms. To support high frame rates, the cameras were connected in pairs to two 4-port Ethernet switches, which in turn were connected to Gb-Ethernet ports on the computer. Images were acquired using custom-built software in Matlab and C++ using the Pylon API (Basler AG, Ahrensburg, Germany), and saved without compression. To allow synchronization of all cameras in the position-tracking and ocular videography systems, the frame signals of each of the position tracking cameras were digitally recorded (Power1401 with Spike2 software, Cambridge Electronic Design, Cambridge England). The oculography cameras did not have a frame synchronization signal, and were instead synchronized using the computer clock times at which the individual frames were recorded combined with periodic modulations of the IR-LEDs used for illumination of the eyes. The voltage driving the modulations of the eye illumination LEDs were recorded on the same analogue to digital converter as the frame synchronization signals from the position-tracking cameras, with the modulations consisting of a slowly increasing ramp (250 ms duration) with a sudden offset occurring ~once per minute.

Analysis Methods

Camera Models

We described the mapping of points in 3D space onto a 2D plane using standard "pinhole" camera models, with perspective projection augmented by nonlinear lens distortion[7]. Three-dimensional points are described using "camera coordinates," with axes along the camera's image plane (x, y) and optical axis (z) and the camera's optical center at the origin. A point $[x\ y\ z]^T$ in camera coordinates is first mapped by perspective projection to coordinates in an idealized image plane:

$$\begin{bmatrix} x \\ y \\ z \end{bmatrix} \to \begin{bmatrix} a \\ b \end{bmatrix} = \begin{bmatrix} x/z \\ y/z \end{bmatrix}.$$

We refer to (a, b) as "ideal image coordinates." Next, the effects of three types of lens distortions are modeled: radial, decentering and thin prism distortions[8]. The effects of these distortions are to nonlinearly shift the point's coordinates in the image plane:

$$\begin{bmatrix} a \\ b \end{bmatrix} \to \begin{bmatrix} \tilde{a} \\ \tilde{b} \end{bmatrix} =$$

$$(1 + K(a^2 + b^2))\begin{bmatrix} a \\ b \end{bmatrix} + (a^2 + b^2)\begin{bmatrix} s_1 \\ s_2 \end{bmatrix} + p_1\begin{bmatrix} 3a^2 + b^2 \\ 2ab \end{bmatrix} + p_2\begin{bmatrix} 2ab \\ a^2 + 3b^2 \end{bmatrix}$$

The parameter K describes radial distortion, $s_1$ and $s_2$ thin-prism distortion, $p_1$ and $p_2$ decentering distortion. An additional scaling step produces the point's coordinates in the acquired image:

$$\begin{bmatrix} \tilde{a} \\ \tilde{b} \end{bmatrix} \to \begin{bmatrix} \hat{a} \\ \hat{b} \end{bmatrix} = \begin{bmatrix} \alpha & \gamma \\ 0 & \beta \end{bmatrix}\begin{bmatrix} \tilde{a} \\ \tilde{b} \end{bmatrix} + \begin{bmatrix} a_0 \\ b_0 \end{bmatrix}$$

where $(a_0, b_0)$ defines the optical center, where the camera's optical axis intersects the image.

We can also invert the above mappings to obtain a 3D vector from an image location. Given a point $(\hat{a}, \hat{b})$ in the image we can calculate $(\tilde{a}, \tilde{b})$ by affine transformation and (a,b) by solving polynomial equations or using a lookup table and interpolation. Then the vector $[a\ b\ 1]^T$ in camera coordinates describes a ray passing from the optical centre into the space in front of the camera, and all points on this ray will appear at the original location $(\hat{a}, \hat{b})$ in the image.

For eye tracking, we also used the weak perspective approximation to the pinhole camera model:

$$\begin{bmatrix} x \\ y \\ z \end{bmatrix} \to \begin{bmatrix} a \\ b \end{bmatrix} = \left(\frac{f}{z_0}\right)\begin{bmatrix} x \\ y \end{bmatrix} + \begin{bmatrix} a_0 \\ b_0 \end{bmatrix}$$

In this simplified linear model, the distance of all imaged objects along the camera's optical axis is assumed to be constant, and the ratio of focal length to this distance $f/z_0$ is a single parameter of the model. Note that it was still necessary to fit a complete pinhole model to the eye cameras in order to determine their locations relative to head-tracking LEDs (see section 'Camera calibration').

Camera Calibration

Both the eye tracking and overhead position tracking cameras required calibration in order to determine the parameters described above for mapping of points in the acquired image into points in 3D space. The calibration process consisted of two stages: internal calibration and external calibration. Internal calibration determines the parameters of the camera model and how 3D space points map to 2D image points, while external calibration determines the locations and orientations of cameras relative to one another or to other relevant objects. Both stages involve minimization of re-projection error, which we performed using a custom implementation of the Gauss-Newton algorithm in Matlab.

Internal calibration of the overhead cameras for position tracking was performed using a grid-based method[9]. A 7×11 checkerboard grid of 2.5 cm black and white squares was positioned by hand at various locations and orientations beneath the 4 overhead cameras under infrared illumination. The grid was detected in each image using a custom-written procedure in Matlab that included sub-pixel corner detection similar to the OpenCV FindCornerSubPix function[10]. About 50 images per camera were then used to estimate the camera parameters, first in a closed-form solution derived from homography fitting and subsequently by minimizing re-projection error of the grid corners[9]. All measurements in pixels or cm were normalized to improve numerical[11]. Since overhead cameras and lenses were manufactured and aligned to precise specifications, we fixed $\alpha=\beta$, and $\gamma$, $s_1$, $s_2$, $p_1$, $p_2=0$, since implementing these parameters does not improve calibration quality in such cases[7]. Enabling these additional parameters produced values of $\alpha$ close to $\beta$ and the other quantities close to zero.

For external calibration of the overhead cameras, we used the fact that during the internal calibration procedure the position and orientation of the checkerboard grid is also estimated in each camera's coordinate system[9]. Therefore a pair of images acquired simultaneously from cameras j and k yields coordinates for each corner of the grid in the two cameras' coordinate systems $g_j$, $g_k$. Both $g_j$ and $g_k$ are 3×77 matrices (assuming all points are visible in both images) and are related by an unknown rotation and translation:

$$g_j = R_k^j g_k + T_k^j.$$

The goal of external calibration is to determine $R_k^j, T_k^j$ since they describe the position and location of camera k in the coordinates of camera j. Combining correspondences from several simultaneously acquired image pairs, we estimated $R_k^j$, $T_k^j$ using singular value decomposition[12]. Finally, a complete minimization of re-projection error over all grid corner points and cameras can be performed, in which grid positions, camera positions, and internal parameters are all adjusted simultaneously. The positions and orientations of the rectangular jumping platforms were then determined by triangulation across all 4 cameras.

Calibration of the eye tracking cameras required a different method because it was not possible to obtain sharp images of a checkerboard grid due to the short focal distance and limited depth of field of the cameras. Instead, we developed a technique based on imaging a known 3D point set[7] to calibrate a complete pinhole camera model for the eye cameras. A single "calibration LED" was mounted on a micromanipulator (MP-285, Sutter Instruments, Novato, Calif., USA) and moved to a grid of locations in 3D space in front of the eye cameras. The calibration LEDs brightness and 3D position were controlled using a custom-written Spike2 script (Cambridge Electronic Design, Cambridge England), and these 3D positions were compared to its positions within the acquired images. For the internal calibration, lens distortion was initially ignored while a closed form solution was obtained for $\alpha$, $\beta$, $\gamma$, $a_0$ and $b_0$. Next, this solution was improved and all lens distortion parameters were determined by minimizing re-projection error. It was necessary to include all lens distortion parameters since the eye cameras were hand assembled with components that may be slightly tilted or off-axis, so that decentering and thin-prism distortions can be present[8].

The goal of external calibration for the eye cameras was to determine their location and orientation relative to the head tracking LEDs, a necessary step for projecting the gaze directions into the environment (see section "Eye tracking"). To achieve this, we used the fact that a 3D point set-based calibration of the eye cameras also determines $R_{MM}^{EC}$, $T_{MM}^{EC}$ describing a rigid body transformation from micromanipulator coordinates to eye camera coordinates[7]. In order to relate the position of objects in the images from the eye tracking cameras to the positions relative to the position tracking LEDs requires simultaneous images of the position tracking LEDs during this calibration process. To achieve this, two Basler "side cameras" were positioned about one meter horizontally from the micromanipulator for observation of the motion of the calibration LED so that rigid body transformations $R_{MM}^{SC}, T_{MM}^{SC}$ from micromanipulator coordinates to both side cameras' coordinates could be obtained. Since the position tracking LEDs were also visible from the side cameras, the location of all position tracking LEDs in side camera coordinates could be determined by triangulation. We used this information to fit a rigid body transformation[12] from the position tracking LED coordinate space to a side camera coordinate space, which we denote $R_{LED}^{SC}, T_{LED}^{SC}$. Finally, we computed:

$$R_{EC}^{LED} = (R_{LED}^{SC})^{-1} R_{MM}^{SC} (R_{MM}^{EC})^{-1}$$

which allows us to map any vector in eye camera coordinates to a vector in position tracking LED coordinates. Since the results of eye tracking consist of vectors in eye camera coordinates, this allows us to map gaze vectors into LED coordinates. By further applying the mapping $R_{head}$ from position tracking LED coordinates to overhead tracking camera coordinates we can subsequently project gaze vectors into the environment (see section 'Head tracking' below).

The weak perspective model used for eye tracking was calibrated using a special procedure using only eye images, which is described below in the section 'Eye tracker calibration.'

Head Tracking

To track the position and orientation of the rat's head, we used an improved version of the infrared videography approach to head tracking used in previous work with freely moving rodents. Head tracking was initialized by manually marking the locations of the position tracking LEDs in the images simultaneously acquired by two or more of the overhead tracking cameras, and determining the pose, consisting of rotation and translation ($R_{head}$, $T_{head}$) that minimized re-projection error. ($R_{head}$, $T_{head}$) define a rigid-body transformation from position tracking LED coordinates to the coordinates of the first overhead camera (referred to as the reference overhead camera in the section 'Calculation of gaze elevation/declination and horizon orientation on the retina below), and from this we can further calculate coordinates for the other cameras by com-posing with each transformation $R_1^j, T_1^j$. Subsequently tracking could proceed automatically both forward and backward in time from the initialization point. For automatic pose estimation at time point i based on the 4 acquired images $I_i^j$ with values in the range of 0-255, we defined an "error image" E, defined at pixel p by:

$$E_i^j[p] = \sum_{p'|D(p,p')\leq r_{LED}} \min(200, \max(0, 250 - I_i^j[p']))(1 - 0.9 \cdot D(p, p')/r_{LED})$$

where D(p,q) is Euclidean distance between pixels p and q, and $r_{LED}$ is the radius of an LED in pixels, which was set to 2. For pixels not 50 grey scale values brighter than a median image, E was set to the maximum possible value. For any given pose (R, T) we can calculate the position of each LED in each image (see section 'Camera Calibration' above), so summing E over the six re-projected LED positions and four cameras gives an error function e(R, T). When calculating e, we sampled E at noninteger coordinates using bilinear interpolation.

We minimized e using a standard Neadler-Mead simplex search[14] as implemented by Matlab's fminsearch function, with the following parameters: tolx=0.0001, tolfun=0.1, maxfunevals=10000, maxiter=10000. We used two candidate head poses to initialize the search: the pose from the previous frame, and the same pose shifted forward by the distance between the two LEDs on the front-facing strut. We chose simplex search as opposed to gradient based methods since the latter occasionally became trapped in local minima (data not shown).

Measurement of Head Tracking Accuracy

To test the accuracy of the head tracking system, we used a rotation stage consisting of 3 goniometers with orthogonal rotation axes which we termed the pitch, roll and yaw axes of the rotation stage. The yaw axis (the axis which was unaffected by yawing rotation) was approximately, but not precisely parallel to the vertical (gravitational) axis of the environment. The head-mount assembly was mounted on the rotation stage, and head tracking was performed as usual using the 6 head-tracking LEDs. The imaging settings (camera system, lenses, exposure time, etc.) were the same as those used for head tracking in freely moving animals, and the distance of the rotation stage from the cameras was the same.

Pitch and roll were varied in increments of 10° from −60° to 60°, while yaw was zero or 90°. We tested the accuracy of our head-tracking system by comparing nominal rotation indicated on the goniometers to rotation detected through our head tracking procedures. However, the detected angles are not expected to be the same since the definitions of pitch, roll and yaw in the head tracking system and rotation stage differ in two important ways:

The orientations of the axes of rotation for pitch, roll, and yaw are different.

The reference orientation, to which a given rotation is compared in order to calculate pitch, roll and yaw is different.

Therefore, we expect the nominal rotation on the rotation stage $R_{Stage}$ and the detected rotation in camera coordinates $T_{Head}$ to be related by the equation:

$$R_{Head} \approx \widehat{R}_{Head} = R_{Stage}{}^{Cam} R_{Stage} (R_{Stage}{}^{Cam})^T R_{Head}{}^Q$$

where $R_{Head}{}^Q$ is the correct value of $R_{Head}$ when nominal pitch, roll and yaw are zero for the rotation stage. $R_{Stage}{}^{Cam}$ maps from the coordinates of the rotation stage to the camera coordinates used for head tracking.

To evaluate the match between nominal and detected rotations, we therefore calculated $R_{Head}$ and $R_{Stage}$ for each orientation, and chose $R_{Head}{}^0$ and $R_{Stage}{}^{Cam}$ to give the best possible match. This fitting step involves 6 free parameters, which we do not expect to lead to overfitting since over 300 orientations were tested. To calculate the quality of the match, we computed the "difference rotation" from the predicted vs. detected rotation in head-tracking (camera) coordinates:

$$R_{diff} = R_{Head} \widehat{R}_{Head}{}^T = R_{Head}(R_{Head}{}^0)^T (R_{Stage}{}^{Cam})^T R_{Stage} {}^T R_{Stage}{}^{Cam}$$

We then defined the head-tracking error $e_{HT}$ as the total rotation of $R_{diff}$ (that is, the angle of its angle-axis representation):

$$e_{HT} = \cos^{-1}\left(\frac{\text{trace}(R_{diff}) - 1}{2}\right)$$

We minimized the sum of $e_{HT}{}^2$ overall orientations, optimizing over Euler-angle representations of $R_{Head}{}^G$ and $R_{Stage}{}^{Cam}$ using Matlab's fminsearch function. This yielded errors of around 1° (root-mean-square error 1.15°). We also decomposed $\widehat{R}_{Head}$ in the same Euler angle representation used to define $R_{Head}$ for head tracking, revealing errors between 0.5° and 1° for each rotation axis (root-mean-square error 0.79° for pitch, 0.89° for roll and 0.55° for yaw).

Eye Tracking Method
Removal of Specular Highlights

In order to perform eye-tracking, it was necessary to remove excessively bright and saturated regions of the eye camera image $I_{eye}$ arising from specular reflections of the eye illumination LED on the cornea. For this purpose we defined two binary images the same size as $I_{eye}$: a "landmark detection mask" for correcting eye displacements relative to the camera (see 'Compensation for lateral eyeball displacement') and a "pupil boundary detection mask" for eye tracking. These binary images contain values of zero where a pixel is contained in a specular highlight and should be ignored, and one otherwise.

First, we defined several linear filters operating on images by convolution, which we denote by the operator '∘'. G is a 15×15 symmetric Gaussian with a width of 5 pixels, defined using the Matlab command fspecial('gaussian',[15 15], 15). H is a 5×5 filter whose entries are all 1 except for the four corner elements which are 0. $F_x$, $F_y$ are 5×5 filters defined by:

$$F_x = \begin{bmatrix} 0 & -0.1715 & 0 & 0.1715 & 0 \\ -0.343 & -0.1715 & 0 & 0.1715 & 0.343 \\ -0.343 & -0.1715 & 0 & 0.1715 & 0.343 \\ -0.343 & -0.1715 & 0 & 0.1715 & 0.343 \\ 0 & -0.1715 & 0 & 0.1715 & 0 \end{bmatrix}, F_y = F_x^T$$

To obtain the landmark detection mask, we first calculated a binary image $B_1$ with nonzero pixels wherever $I_{eye} \circ G >$ median $(I_{eye}) \cdot \lambda_1$, where $\lambda_1$ is a user-adjustable threshold set to 2.5 for most imaging sessions. We then operated on $B_1$ by a morphological closing operation followed by an opening operation, both using a 10 pixel radius disk as a structuring element, to produce $B_2$. Finally we defined the landmark detection mask by $$B_L = \neg (B_1 \wedge B_2)$$

where ¬, ∧ denote pixel-wise logical NOT and AND respectively.

To obtain the pupil boundary detection mask, we first calculated:

$$I_\delta = (I_{eye} \circ G \alpha F_x)^2 + (I_{eye} \circ G \circ F_y)^2$$

We then calculated a binary image $B_3$ with nonzero pixels wherever:

$$I_{eye} \circ G > \text{median}(I_{eye}) \cdot \lambda_2 \vee I_\delta > \text{median}(I_\delta) \cdot \lambda^2{}_3$$

with $\lambda_2$ set to 1.5 and $\lambda_3$ set to 3.5 for most imaging sessions and ∨ denoting logical OR. We then calculated $B_4$ by morphological closing followed by opening with a 10 pixel disk, and define the pupil boundary detection mask by $$B_P = \neg (B_3 \wedge B_4).$$

Calculation of Gradients in Eye Images

Eye tracking required calculation of image gradients $I_x$ and $I_y$ since the pupil detection scheme (see 'Eye tracking' below) is designed to identify a dark-to-light transition at the pupil boundary. Direct differences of adjacent pixel values produced gradient values that were too noisy for eye tracking, so it was necessary to incorporate pixel values from a larger surrounding window in the calculation. However, this required specially normalized calculations to deal with the fact that some pixel values had to be ignored due to specular highlights. We used the following normalization scheme (multiplications without the convolution symbol '∘' are pixel-wise; see previous section 'Removal of specular highlights' for filter and mask definitions):

$$M_{eye} = \frac{B_P I_{eye} \circ H}{B_P \circ H}$$

$$M_x = \frac{B_P \circ F_x}{B_P \circ H}, M_y = \frac{B_P \circ F_y}{B_P \circ H}$$

$$V_x = \frac{B_P \circ (F_x)^2}{B_P \circ H} - M_x^2, V_y = \frac{B_P \circ (F_y)^2}{B_P \circ H} - M_y^2$$

$$I_x = \left(\frac{B_P I_{eye} \circ F_x}{B_P \circ H} - M_{eye} M_x\right) / V_x,$$

$$I_x = \left(\frac{B_P I_{eye} \circ F_y}{B_P \circ H} - M_{eye} M_y\right) / V_y$$

$M_{eye}$, $M_x$ and $M_y$ compute local means for the image and gradient filters given the pupil boundary detection mask $B_P$, while $V_x$, $V_y$ compute variances for the filters. The subsequent calculation of gradients ultimately computes a regression coefficient (slope) for $I_{eye}$ as a function of image coordinates over a neighborhood of pixels around each point, ignoring pixels for which $B_P=0$.

Compensation for Lateral Eyeball Displacement—Tracking of Anatomical Landmarks Around the Eye Before performing eye tracking, we first detected and compensated for translations of the eye parallel to the image plane (translations parallel to the optical axis have no effect in a weak perspective camera model). First, a point in the medial corner of the eye (near the tear duct) was marked manually in one more image frames. A 150×150 pixel region was extracted from the image around the marked point in each image and divided by the median pixel value across the entire image. These normalized sub-images were then averaged across the manually marked images to generate a template, while ignoring pixels for which the landmark detection mask was zero.

After creating the template, we detected lateral shifts in the position of the corner of the eye automatically by comparing the template to the eye camera image. We divided the image by its median and then determined the shift in pixel coordinates that minimized the mean square difference between template and image, again ignoring pixels for which the landmark detection mask was zero. For imaging sessions in which the lateral junction of the eyelids (lateral canthus) was clearly visible, it was tracked by a second template and the mean square differences from the two were added together and minimized to determine lateral shifts.

Using this method we detected a lateral shift in pixel coordinates for each frame relative to the first frame used for template generation. We subtracted this shift from all subsequent pixel coordinates in each frame, so that the positions of the center of the eyeball (see below) and tear duct in these corrected coordinates was constant.

Eye Tracking

The goal of eye tracking is to determine the 3D rotation of the eye by analyzing the position and shape of the pupil boundary. While the pupil is actually circular, it appears in the eye camera images as an ellipse due to misalignment of the pupil and the image plane. Our strategy is to define an objective function $O$ that evaluates how well a given choice for the pupil boundary matches the image $I_{eye}$ acquired by the eye camera, and then to determine the eye rotation $R_{eye}$ that maximizes $O$ the objective function. This requires a geometric model of the eye combined with a camera model, for which we chose weak perspective (described in the section 'Camera models' above).

The objective function $O$ is based on the idea that the pupil appears darker than the surrounding iris, so that the gradient of the image along an outwardly oriented normal vector to the pupil boundary will be positive (see 'Calculation of gradients in eye images' above). The elliptical pupil boundary is described by its center $[a_{PC}\ b_{PC}]^T$, major axis length L, minor axis length l and inclination $\omega$. The following affine transform maps points q on the unit circle onto the pupil boundary:

$$q \to q^* = \begin{bmatrix} \cos\omega & -\sin\omega \\ \sin\omega & \cos\omega \end{bmatrix} \begin{bmatrix} L & 0 \\ 0 & l \end{bmatrix} q + \begin{bmatrix} a_{PC} \\ b_{PC} \end{bmatrix}$$

We denote $q_m$ for $0 \le m < N_{circ}$ by $[\cos(2\pi m/N_{circ}), \sin(2\pi m/N_{circ})]^T$ and set $N_{circ}=100$, so that $\{q_m\}$ are a set of 100 equally spaced points around the unit circle and their destinations $\{q_m^*\}$ under the above affine mapping are distributed over the pupil boundary in the image. Representing the input to the affine mapping in polar coordinates and taking the derivative reveals that the unit vector normal to the pupil boundary at $q_m^*$ is:

$$n_m = \frac{1}{\sqrt{L^2\sin(2\pi m/N_{corc})^2 + l^2\cos(2\pi m/N_{circ})^2}} \begin{bmatrix} L\sin\omega\sin(2\pi m/N_{circ}) - \\ l\cos\omega\cos(2\pi m/N_{circ}) \\ L\cos\omega\sin(2\pi m/N_{circ}) - \\ l\sin\omega\cos(2\pi m/N_{circ}) \end{bmatrix}$$

Using this result, the objective function is defined for any ellipse as the sum of dot products:

$$O(a_{PC}, b_{PC}, L, l, \omega) = \sum_{m=0}^{N_{circ}-1} n_m \cdot \begin{bmatrix} I_x[q_m^*] \\ I_y[q_m^*] \end{bmatrix}$$

In order to use this objective function for eye tracking, it was next necessary to describe how the elliptical pupil boundary depends on eye rotation $R_{eye}$ and pupil diameter r. We modeled the eye as a sphere and the pupil boundary as a disk with center at a fixed distance from the eye center. We termed this distance the "pupil rotation radius". For simplicity we used the pupil rotation radius as the unit for distance when describing any location relative to the eyeball center. We define the "gaze vector" w as the unit vector passing from the eyeball center to the pupil center. Thus a gaze vector of $[0\ 0\ -1]^T$ in eye camera coordinates would point directly toward the optical center of the eye camera, causing the pupil center to appear directly in front of the eyeball center at some image coordinates $[a_{EC}, b_{EC}]^T$. We term this "the reference position of the eye," where the pupil boundary consists of points $[u, v, -1]^T$ relative to the eyeball center in camera coordinates, with $u^2+v^2=r^2$.

We calculated the location and shape of the pupil boundary in the eye camera image as a function of eye camera rotation. Any orientation of the eye can be described by a rotation from its reference position, which we decompose:

$$R_{eye} = R_\phi R_\theta R_\psi = \begin{bmatrix} 1 & 0 & 0 \\ 0 & \cos\phi & \sin\phi \\ 0 & \sin\phi & \cos\phi \end{bmatrix} \begin{bmatrix} \cos\theta & 0 & -\sin\theta \\ 0 & 1 & 0 \\ \sin\theta & 0 & \cos\theta \end{bmatrix} \begin{bmatrix} \cos\psi & \sin\psi & 0 \\ \sin\psi & \cos\psi & 0 \\ 0 & 0 & 1 \end{bmatrix}$$

The angles $\phi$, $\theta$, and $\psi$ describe vertical, horizontal, and torsional rotations, respectively. Since torsional rotation around the gaze vector has no effect on the appearance of the circular pupil boundary, we ignore it and set $\psi=0$ for now (but see section 'Detection of ocular torsion' below). The rotation maps the gaze vector from the reference position to the new position:

$$\begin{bmatrix} 0 \\ 0 \\ -1 \end{bmatrix} \to w = \begin{bmatrix} \sin\theta \\ \sin\phi\cos\theta \\ -\cos\phi\cos\theta \end{bmatrix}$$

which projects through the weak perspective camera model to the location of the pupil center in the image:

$$\begin{bmatrix} a_{PC} \\ b_{PC} \end{bmatrix} = \frac{f}{z_0}\begin{bmatrix} \sin\theta \\ \sin\phi\cos\theta \end{bmatrix} + \begin{bmatrix} a_{EC} \\ b_{EC} \end{bmatrix}$$

Similarly, rotation followed by projection maps the circular pupil boundary with radius r into the following ellipse:

$$\begin{bmatrix} u \\ v \\ -1 \end{bmatrix} \to \begin{bmatrix} a_{PC} \\ b_{PC} \end{bmatrix} + \frac{f}{z_0}\begin{bmatrix} \cos\theta & 0 \\ -\sin\theta\sin\phi & \cos\phi \end{bmatrix}\begin{bmatrix} u \\ v \end{bmatrix}$$

The norm of the second term is maximized for:

$$\begin{bmatrix} u \\ v \end{bmatrix} = \pm\frac{r}{\sqrt{1-w_3^2}}\begin{bmatrix} -\sin\phi \\ \cos\phi\sin\theta \end{bmatrix}$$

and minimized for:

$$\begin{bmatrix} u \\ v \end{bmatrix} = \pm\frac{r}{\sqrt{1-w_3^2}}\begin{bmatrix} \cos\phi\sin\theta \\ \sin\phi \end{bmatrix}$$

Mapping these points on the pupil boundary into the image shows that the ellipse has major axis length $$r\frac{f}{z_0}$$

minor axis length $$|w_3|r\frac{f}{z_0}$$

and inclination $\tan^{-1}(\tan 0/\sin 0)$ and that the minor axis lies on the line connecting the pupil center to the eyeball center. Thus assuming we know $$\begin{bmatrix} a_{EC} \\ b_{EC} \end{bmatrix} \text{ and } \frac{f}{z_0}$$

(see section 'Eye tracker calibration' below) then for any combination of rotation and pupil radius we can calculate the position of the pupil boundary in the image, and conversely for any pupil boundary location we can calculate $\phi$, $\theta$, r and the gaze vector w.

We used this correspondence to compute our objective function on ellipses as a function of eye rotation and pupil radius $O(\phi,\theta,r)$. This representation of $O$ has three main ad-vantages: the dimension of the optimization problem is reduced from 5 to 3, all detected pupil boundaries will be realizable by some eye rotation and pupil dilation/contraction, and the re-placement of abstract ellipse parameters with real-world rotations and distances allows realistic physical limitations to be imposed on each parameter's rate of change. Based on previous studies in the rat that delivered a strong light stimulus or direct electrical stimulation of the ciliary muscle, we imposed a maximum contraction/dilation rate of 2%/frame. Together with this, we imposed a maximum rotation of 25°/frame or 1250°/sec., the validity of which we also checked by visual inspection of the imaging.

These constraints allowed direct, non-iterative maximization of $O$ by exhaustive search over $(\phi,\theta,r)$. We first maximized $O$ by varying the $(\phi,\theta)$ in increments of 2° over the allowed range and r in increments of 2%. At the detected maximum, we performed an additional local search over a region of 4.4°×4.4°×2.2% in increments of 0.5° and 0.5%. We then performed a third search at the new maximum over a region of 1°×1°×1% in increments of 0.1° and 0.1%, to produce the final estimates of eye rotation, pupil diameter, and pupil boundary location for the given image frame.

Eye Tracker Calibration

The eye tracking method described above requires determination of the image coordinates $[a_{EC}, b_{EC}]^T$ of the eye center and the scaling factor $f/z_0$. We therefore developed a calibration procedure to estimate these quantities using only a sequence of images of the eye. This calibration procedure requires at least two eye camera frames for which the elliptical pupil boundary has been detected in the image. In practice we used >30 calibration frames per imaging session, and for these few dozens of frames the pupil boundary was marked either manually or automatically by maximizing $O$ over ellipses through simplex search.

The calibration procedure is based on the following observations:

The point $$\begin{bmatrix} a_{EC} \\ b_{EC} \end{bmatrix}$$

can be found on the intersection of the lines containing the minor axes of all pupil boundary ellipses (see section 'Eye tracking' above).

The third element of the gaze vector w can be calculated as a ratio of minor:major axis lengths $w_3=-l/L$.

Subtracting $$\begin{bmatrix} a_{EC} \\ b_{EC} \end{bmatrix}$$

from any ellipse center gives:

$$\frac{f}{z_0}\begin{bmatrix} \sin\theta \\ \cos\theta\sin\phi \end{bmatrix} = \frac{f}{z_0}\begin{bmatrix} w_1 \\ w_2 \end{bmatrix}.$$

The norm of this difference vector is:

$$\frac{f}{z_0}\sqrt{w_1^2 + w_2^2} = \frac{f}{z_0}\sqrt{1 - w_3^2}.$$

Since we know $w_3$ from step (ii), we can compute $f/z_0$.

Based on these observations we implemented a procedure that incorporated multiple pupil boundary ellipses with parameters $(a_{PC}^i, b_{PC}^i, L^i, l^i, \omega^i)$ to robustly estimate $$\begin{bmatrix} a_{EC} \\ b_{EC} \end{bmatrix} \text{ and } \frac{f}{z_0}.$$

The fact that $$\begin{bmatrix} a_{PC}^i \\ b_{PC}^i \end{bmatrix} - \begin{bmatrix} a_{EC} \\ b_{EC} \end{bmatrix}$$

is orthogonal to unit vector $$\begin{bmatrix} \cos\omega^i \\ \sin\omega^i \end{bmatrix}$$

along the major axis gives the linear constraint:

$$a_{EC}\cos\omega^i + b_{EC}\sin\omega^i = a_{PC}^i\cos\omega^i + b_{PC}^i\sin\omega$$

for each i. Combining these constraints for many images gives an overdetermined system, for which the least squares solution was used to estimate $$\begin{bmatrix} a_{EC} \\ b_{EC} \end{bmatrix}.$$

For each image we calculated:

$$\sqrt{1-(w_3^i)^2} = \sqrt{1-(l^i/L^i)^2}$$

From which:

$$\left\| \begin{bmatrix} a_{PC}^i \\ b_{PC}^i \end{bmatrix} - \begin{bmatrix} a_{EC} \\ b_{EC} \end{bmatrix} \right\| = \frac{f}{z_0}\sqrt{1-(w_3^i)^2}$$

so we calculated the least squares solution:

$$\frac{f}{z_0} = \frac{\sum_i \sqrt{1-(l^i/L^i)^2} \left\| \begin{bmatrix} a_{PC}^i \\ b_{PC}^i \end{bmatrix} - \begin{bmatrix} a_{EC} \\ b_{EC} \end{bmatrix} \right\|}{\sum_i 1-(l^i/L^i)^2}$$

The next step of the eye tracker calibration required minimizing re-projection error for the pupil boundary. Because we are comparing ellipses instead of points, it was first necessary to define a dissimilarity metric for comparing two ellipses. For each ellipse we computed five points: the center, and points on the ellipse oriented 0, 45, 90, and 135 degrees from the center relative to the positive horizontal axis of the eye image. We then defined the dissimilarity between two ellipses as the square Euclidean distance summed over these five points.

We next determined eye rotation and pupil radius ($\phi^i$, $\theta^i$, $r^i$) for each image using a simplex search to minimize re-projection error between the rotated and projected pupil boundaries (see section 'Eye tracking' above) and the pupil boundaries marked in the calibration frames. Finally, we performed a nested simplex search over all ($\phi^i$, $\theta^i$, $r^i$) as well as ($a_{EC}$, $b_{EC}$, $f/z_0$) simultaneously. Specifically, for any choice of ($a_{EC}$, $b_{EC}$, $f/z_0$) all values ($\phi^i$, $\theta^i$, $r^i$) were determined by individual simplex searches in each frame, and re-projection error was summed over i to give a function on ($a_{EC}$, $b_{EC}$, $f/z_0$). This function was then minimized by a simplex search in 3 dimensions. This procedure allowed us to minimize re-projection error over ($a_{EC}$, $b_{EC}$, $f/z_0$) as well as the eye rotation and pupil radius in all calibration frames simultaneously without having to perform a simplex search in more than 3 dimensions at once.

Estimation of Error in Pupil Detection Method

To verify the accuracy of the eye tracking method, we used a model eye consisting of an iron ball 7.15 mm in diameter with a painted black disk 1.15 mm diameter to represent the pupil. We moved the ball using a rotational micromanipulator with a sensitivity of 1° in the range of −10° to +10° along both vertical and horizontal axes, while recording with one eye camera. Lighting conditions were adjusted to approximate those used for eye tracking. We were able to detect rotational displacements of the iron ball with an error of 0.9°±0.1° and estimate the pupil radius with an error of 0.078±0.005 mm.

Estimation of Anatomical Landmark Tracking Error

Given the dependence of the calculated eye angles on the location of the eye ball center, and the dependence of the eyeball center on the detected eye corner position, we also assessed the influence of displacements of the tracked eye corner position on the computed eye angles. For this purpose ten images were selected at random for each eye from datasets from 3 animals. For each image, the originally tracked eye corner position, pupil location in the image in pixel coordinates and eye rotation angles were stored, and the corner position was then dis-placed by a fixed number of pixels in a randomly-selected angle. The pupil location and eye rotation angles were then computed again, using the displaced corner position. The effects of radial displacements of 2, 5, 10, 20 and 30 pixels were analyzed. Pupil displacements were made in a total of 20 different angles for each radius for each image, with one set of randomly-chosen angles being used for both left and right eye images from one dataset. For each displacement, the Euclidean distance to the originally tracked pupil location was calculated, as well as the difference between the originally calculated horizontal and vertical eye rotation angles and those resulting after corner displacement.

Detection of Ocular Torsion

Having calibrated the eye tracker and detected eye rotations ($\phi$, $\theta$) and radius r for each frame, we next implemented a procedure to detect ocular torsion. The torsion $\psi$ is a rotation of the eye around the gaze vector. While rotation of a circular pupil boundary would have no effect on the appearance of the boundary in the image, in reality the pupillary margin is not perfectly circular, having a slightly uneven, crenelated edge (FIG. 15c). When the pupil is in the reference position (i.e. $\phi$, $\theta$, $\psi$=0), the boundary can be described in polar coordinates as a distance from the pupil center as a function of angle:

$$s(\tau) = r(1 + U(\tau))$$

where r is the time-varying radius of a circular approximation to the boundary and $U(\tau)$ is a time-independent function of angle with values around 0. Applying the rotation $R_{eye} = R_\phi R_\theta R_\psi$, and projecting through the weak perspective camera model gives a polar form for the pupil boundary in the image:

$$\tau \rightarrow \begin{bmatrix} a \\ b \end{bmatrix} = \begin{bmatrix} a_{PC} \\ b_{PC} \end{bmatrix} + \frac{f}{z_0} \begin{bmatrix} \cos\theta & 0 \\ -\sin\theta\sin\phi & \cos\phi \end{bmatrix} \begin{bmatrix} \cos\psi & -\sin\psi \\ \sin\psi & \cos\psi \end{bmatrix} s(\tau) \begin{bmatrix} \cos\tau \\ \sin\tau \end{bmatrix} =$$

$$\begin{bmatrix} a_{PC} \\ b_{PC} \end{bmatrix} + r(1+U)(\tau)\frac{f}{z_0} \begin{bmatrix} \cos\theta & 0 \\ -\sin\theta\sin\phi & \cos\phi \end{bmatrix} \begin{bmatrix} \cos(\tau+\psi) \\ \sin(\tau+\psi) \end{bmatrix}$$

To estimate U and to determine $\psi$ for each frame, we first used this mapping while setting $\psi=0$ to obtain pixel values across a map of the pupil plane in polar coordinates:

$$I(\rho,\tau) = I_{eye}\left[a_{PC} + \rho r \frac{f}{z_0}\cos\tau\cos\theta, b_{PC} + \rho r \frac{f}{z_0}(\sin\tau\cos\phi - \cos\tau\sin\theta\sin\phi)\right]$$

The pupil boundary appears on this map as the curve with polar coordinates $(1+U(\tau-\psi),\tau)$, while the circular approximation to the pupil boundary has coordinates $(1,\tau)$.

A simple strategy for detecting ocular torsion can then be summarized as follows:
(i) In each frame i, detect in $I(\rho,\tau)$, a dark-to-light transition in the direction of increasing $\rho$ at each $\tau$, yielding a curve $(1+\hat{U}_i(\tau),\tau)$
(ii) Compare the detected curves for two successive frames to calculate $$\psi_{i+1} - \psi_i = \underset{\psi}{\operatorname{argmax}} \operatorname{Corr}_\tau(\hat{U}_i(\tau-\psi), \hat{U}_{i+1}(\tau))$$

Our actual implementation differed from this simple strategy by also introducing a template $\overline{U}(\tau)$ and by filtering the curves before calculating correlation.

We first computed $I(\rho,\tau)$ over a grid of polar coordinates $(\rho,\tau)$, with $\rho$ ranging from 0.75 to 1.25 in increments of 0.002, and $\tau$ from 0 to 360° in increments of 0.5°. To detect $(1+\hat{U}_i(\tau),\tau)$, we first applied a Gaussian filter to $I(\rho,\tau)$ along the $\rho$ axis with a standard deviation of 10 points (or 0.02 in units of $\rho$), while ignoring points that mapped into regions of $I_{eye}$ where the pupil boundary detection mask was zero (see section 'Removal of specular highlights' above). Denoting this filtered map $I_G(\rho,\tau)$, we then defined, $\chi(\tau)$ as the median of $I_G(\rho,\tau)$ across $\rho$ values for each value of $\tau$. We then filtered, $\chi(\tau)$ to produce $\chi_L(\tau)$ using a lowpass filter with cut-off frequency 0.011 degrees$^{-1}$ (cutoff period 90°) designed using Matlab's fir1 function with order 359. Then for each $\tau$, the pupil boundary radius $1+\hat{U}_i^{raw}(\tau)$ was detected as the minimum value of $\rho$ for which $$I_G(\rho,\tau) = \chi_L(\tau)$$

Linear interpolation was used to find the value of $\rho$ where this equality held precisely. We then obtained $U_i(\tau)$ by filtering $\hat{U}_i^{raw}(\tau)$ with a bandpass filter with passband from 0.033 to 0.2 degrees$^{-1}$ (periods of 5° to 30°), again using fir1 with order 359. When filtering $\hat{U}_i^{raw}(\tau)$ to produce $\hat{U}_i(\tau)$, we used only segments of the curve where $-0.1 \leq \hat{U}_i^{raw}(\tau) \leq 0.125$, leaving other segments undefined.

The first frame analyzed in this manner was assigned a torsion $\psi=0$ (but see section 'Head and eye coordinate systems' below for an anatomically inspired correction introduced subsequently). We used the first detected boundary as a template $\hat{U}(\tau)$ to detect torsion in several additional "torsion calibration frames" by maximizing $\operatorname{Corr}_\tau(\overline{U}(\tau-\psi), \overline{U}_i(\tau))$, the Pearson's correlation over $\tau$ between each frame's detected boundary and a rotated version of the template. We then updated the template using these newly detected torsion values, setting $$\overline{U}(\tau) = \langle \hat{U}_i(\tau+\psi_i) \rangle$$

where $\langle \ldots \rangle_i$ denotes a mean over i. This new template was then used to update torsion values for all torsion calibration frames, including the original source for the template. After several rounds of updating, $\overline{U}(\tau)$ was finalized and used throughout the remainder of the imaging session. We used about 60 torsion calibration frames per imaging session.

Head and Eye Coordinate Systems

In the above sections eye positions movements were described by rotation from a reference position pointing directly into the camera, while head movements were described by rotation and translation from position tracking LED coordinates in a reference space. However, these reference positions may vary arbitrarily across experiments, since the position of the eye camera relative to the eye and the position of head tracking LEDs relative to the head will depend on the precise position and orientation of the head plate attached during surgery and the rotation of the mounting device for the oculography system on the head plate. Since both of these may vary slightly across animals, the meaning of a 5° upward eye rotation or a 10° down-ward head rotation as defined above may not be the same in each experiment.

We therefore developed a procedure to determine coordinate systems and reference positions for the eyes and head that depended only on the animal's anatomy, and not on the placement of the head mount. The basic idea of this procedure was to fit an ellipse to the boundary of each eyelid, and to obtain 3D positions for the tear duct and lateral commissure relative to the eye center based on the intersections of these ellipses.

We modeled the eyelid boundary as a circular arc arising from the intersection of a sphere and a plane. The sphere was located at the pupil's center of rotation but had a $r_{eye}$ radius greater than the pupil rotation radius. The plane was assumed to always pass through two points that were fixed relative to the eye center: the tear duct and the lateral commissure. The remaining one degree of freedom in the plane orientation allows opening and closing of each eyelid to be modeled.

Several frames with varying amounts of eyelid closure were manually selected. In these frames, several points (a, b) along each eyelid were then marked manually, and once five points had been marked on each eyelid the parameters of the algebraic ellipse representation $$Aa^2 + Bab + Cb^2 + Da + Eb + F = 0$$

were obtained were by minimizing $$\{(Aa^2 + Bab + Cb^2 + Da + Eb + F)\}$$

The intersection of ellipses from the upper and lower eyelids yielded the position of the tear duct and lateral commissure in the image. Subtracting the eyeball center $(a_{EC}, b_{EC})$ and dividing by $f/z_0$ then gives the x and y difference of these fixed points from the eye center in eye camera coordinates. The z coordinates of the tear duct and lateral commissure relative to the eye center can then be calculated $$\Delta z = -\sqrt{r_{eye}^2 - \Delta x^2 - \Delta y^2}$$

Therefore, while keeping the x and y coordinates of the tear duct and lateral commissure constant, we minimized the re-projection error between the manually marked points and the eyelid boundary ellipses while varying $r_{eye}$ and the normal vectors of the eyelid planes. This minimization problem involved 2 free parameters per frame as well as $r_{eye}$, so it was over con-strained given 5 or more manually marked points on the upper and lower eyelids. We typically used 2 or 3 frames in this procedure, and about 20 marked points per eyelid.

We next defined a new coordinate system for the eye (eyelid reference system). The eye center was chosen for the origin. The first coordinate axis, the "forward eye axis", was defined as the unit vector in the plane defined by the eye center, tear duct and lateral commissure that lay midway between unit vectors in the same plane pointing toward the tear duct and lateral commissure. The "right eye axis" was chosen to point toward the animal's right side, while lying in the same plane and orthogonal to the forward eye axis. The "dorsal eye axis" points in the dorsal direction and was orthogonal to the other two axes. According to this definition ocular torsions of the right and left eyes take a positive sign when they are counterclockwise and clockwise, respectively.

Having defined coordinate systems for each eye we next defined coordinates relative to the animal's head. For each eye we used $R_{EC}^{LED}$ (see section 'Camera calibration' above) to map the forward eye axis into position tracking LED coordinates, averaged the two results, and normalized to obtain a unit vector which we termed the "forward head axis." Performing the same operation on the dorsal eye axes while removing the component parallel to the forward head axis before normalization yielded the "dorsal head axis." The "right head axis" is then obtained by orthogonality to the other two. Finally, we rotated the forward head axis downwards and the dorsal head axis forward by 36.6°, so that the average elevation of the gaze vector in these coordinates across all animals and imaging sessions would be 30° as measured for the rat[16]. This produced the final reference frame from the head, and the head rotations were ex-pressed based on the mapping from this frame to environmental coordinates with the z axis both perpendicular to the platform and parallel to gravity and the x axis parallel to the long edge of the jumping platforms.

Lastly, we defined an "adjusted reference position for the eye" that did not depend on camera placement. The gaze vector was chosen to lie directly on the forward eye axis, so it remained only to specify a reference torsion. To do this, we identified for each time point the pair of opposite points on the pupil boundary which formed a line segment parallel to the plane jumping platforms, and stored the location of the point on the along the torsion tracking template. We next took the median of these over all time points to identify a single point on the pupil boundary. We then placed this point directly along the right eye axis relative to the pupil center in the reference position. Finally, for any eye position we then decomposed the rotation matrix that mapped this new reference position to the observed eye position into three Euler angles as previously (see section 'Eye tracking' above). This adjusted reference eye position was the fixed position used when calculating the horizon stabilizing effects of eye movements in the presence of ongoing head movements (FIG. 6; see also section 'Calculation of gaze elevation/declination and horizon orientation on the retina' below).

Predictive Eye Position Model

In order to examine the extent to which eye position could be determined by head position, we compared observed eye positions to predicted eye positions based on several simple predictive models. We first considered simple linear regression of horizontal head and vertical eye angles against head position data:

$$\theta = JQ$$

where $\theta$ is a vector of $N_{reg}$ eye positions, J is an $N_{reg} \times 13$ matrix of explanatory variables, and Q is an unknown 13-element vector of regression coefficients. The columns of J were pitch, roll and yaw in the head coordinate system (see section 'Head and eye coordinate systems'), the derivatives of pitch, roll and yaw, the translation $T_{read}$ from position tracking LED coordinates to camera coordinates, the derivatives of $T_{head}$ and finally a column of ones to allow for a constant term in the regression. J was determined by least squares minimization of $\theta - JQ$, using Matlab's '\' operator. We tested the accuracy of this simple linear regression approach using 10-fold cross validation: the data of each recording session was divided into 10 parts, and for each part Q was determined from the other 9 parts and tested on the one excluded part. In this manner we analyzed 7 periods of free movement, arising from 6 imaging sessions in 3 animals. The periods of movement contained between 8296 and 24692 time points, with an average of 14759.0±15 5845 (mean±s.d.). To evaluate the accuracy of prediction, we used the reduction of variance of the residual $\theta - JQ$ as a fraction of the variance of the variable $\theta$ to be predicted:

$$\%\text{Variance Reduction} = 100\left(1 - \frac{\text{Var}(\theta - JQ)}{\text{Var}(\theta)}\right)$$

Thus when the regression perfectly predicts the eye position the variance reduction will be 100%, whereas if the regression were always to output a single repeated value the variance reduction would be 0%. Using this approach, we observed variance reductions of 59.8%±3.8%, 73.8%±2.6%, 65.2%±2.4% and 73.7%±1.8% for the left eye horizontal, left eye vertical, right eye horizontal, and right eye vertical respectively (n=7).

We next attempted to increase the accuracy of our linear predictor by adjusting the coordinate system used to represent rotation of the head. We first calculated for each time point the 3×3 matrix representation $R_{head}$ of head rotation from the first 3 columns of J. We next multiplied $R_{head}$ by a matrix $R_{adj}$ that was constant for all time points, and parameterized by two Euler angles $\alpha_{adj}$, $\beta_{adj}$ (a third Euler angle was not used, since it would merely serve to additively shift one Euler angle describing head rotation by a constant magnitude for all frames, which has no effect for a linear regression). Finally, we then decomposed the product $R_{adj} R_{head}$ into 3 Euler angles, which then replaced the first 3 columns of J. Thus for any choice of $\alpha_{adj}$, $\beta_{adj}$ we can repeat the procedures of the previous model and calculate the cross-validated variance reduction. To maximize the variance reduction over $\alpha_{adj}$, $\beta_{adj}$, we used Neadler-Mead simplex search as implemented by Matlab's fminsearch function. $\alpha_{adj}$ and $R_{adj}$ were thus determined once for each period of free movement. This approach resulted in slight increases in variance reduction, yielding 61.5%±9.4%, 75.5%±6.0%, 65.6%±6.1% and 74.5%±5.2%. While these increases were only about 0.5% to 1.5%, the change was nonetheless statistically significant over the 7 periods test (P<0.05, one-tailed t-tests). Consistent with the small size of this change, the optimal rotations $\alpha_{adj}$, $\beta_{adj}$ were also small, with most values less than 5°. In other words, the coordinate system we used to describe head rotation was nearly optimal for linear prediction of eye movements.

We next attempted to further increase prediction accuracy based on the idea that eye positions may not instantly attain their equilibrium position for a given head position. To implement these ideas, we considered models of the form:

$$\theta_t = \theta_{t-\Delta dt} - \frac{\Delta dt}{\tau}(\theta_{t-\Delta dt} - J_t Q)$$

In this model the eye position decays toward the equilibrium position determined by head position with time constant $\tau$. Note that setting $\tau=\Delta t$ yields the previously considered model. We tested this model using cross-validation as previously described, while maximizing variance reduction of $\alpha_{adj}$, $\beta_{adj}$ and $\tau$. However, this yielded values of $\tau$ close to $\tau t$ and did not increase variance reduction (data not shown). Thus for the achieved imaging rates of 150 Hz, taking into account non-equilibrium dynamics did not improve linear prediction.

Finally, we considered a regression scheme in which a linear regression on angle was followed by a linear regression on vectors, normalization back to unit vectors, and conversion back to angles. This method employed a greater number of parameters, and used as columns of J only pitch, roll and a column of ones. We defined:

$$\widetilde{\theta_L} = JQ_L \quad \widetilde{\theta_R} = JQ_R \quad v_L = V(\widetilde{\theta_L}) \quad v_R = V(\widetilde{\theta_R})$$

where $$V(\theta) = \begin{pmatrix} \sin\theta_1 \\ \cos\theta_1 \sin\theta_2 \\ -\cos\theta_1 \sin\theta_2 \end{pmatrix}.$$

We further defined:

$$\widetilde{V_L} = Av_L + Bv_R + v_L^0 \quad \widetilde{V_R} = Cv_L + Dv_R + v_R^0$$

$$\theta_L^* = V^{-1}\left(\frac{\widetilde{V_L}}{|\widetilde{V_L}|}\right) \quad \theta_R^* = V^{-1}\left(\frac{\widetilde{V_R}}{|\widetilde{V_R}|}\right)$$

where A,B,C,D are 3×3 matrices. We chose $Q_L$, $Q_R$, A, B, C, D, $v_L^0$ and $v_R^0$ to minimize the least-squares error between $\theta_L^*$, $\theta_R^*$ and the observed eye positions, cross validating as above. Predicted eye movements are compared to true eye movements for a segment of data in FIG. 5a. This approach lead to variance reductions of 67.5%±4.5%, 79.8%±3.3%, 70.6%±3.6% and 78.0%±1.3% for the left eye horizontal, left eye vertical, right eye horizontal, and right eye vertical respectively (n=7), which are presented in FIG. 5b as single averages for horizontal and vertical eye positions.

Relative Pupil Position Analysis

The angular displacements of the eye are calculated as rotations of the eye from a reference position (see section 'Eye tracking'). In this system, positive horizontal rotations ($\theta$) have been defined as rotations toward the animal's left and positive vertical rotations ($\phi$) as dorsal eye rotations. For analysis of relative pupil positions, the relative pupil coordinates were calculated as:

$$\theta_{rel} = \theta_{right} - \theta_{left}$$

$$\phi_{rel} = \phi_{right} - \phi_{left}$$

Calculation of the animal's binocular field

Using the measurements of the rat's eye described in[16], we approximated the monocular field of view as a half sphere whose base is perpendicular to the gaze vector, representing a collection angle of ~180 degrees, slightly less than the collection angle estimated for the rat[16] and considered the two eyes to have the same center (a valid approximation when the distance between the eyes is small compared to the distance from the eyes to a viewed object). First we computed the binocular field in the head reference system, where the gaze vectors $g_{left}$ and $g_{right}$ depend only on the eye movements. We considered the grid of equi-spaced angles:

$$\begin{cases} \vartheta = -\pi : \Delta\vartheta : \pi \\ \varphi = -\frac{\pi}{2} : \Delta\varphi : \frac{\pi}{2} \end{cases}$$

$$\Delta\theta = \Delta\varphi = 1°$$

and for each pair of angles on this grid we calculated the vector:

$$v_{jk} = \begin{bmatrix} \cos\vartheta_j \cos\varphi_k \\ \sin\vartheta_j \cos\varphi_k \\ \sin\varphi_k \end{bmatrix}$$

the binocular field was then defined as the subset of grid points (j, k) for which:

$$v_{jk} \cdot g_{left} \geq \cos\frac{\alpha_c}{2}$$

$$v_{jk} \cdot g_{right} \geq \cos\frac{\alpha_c}{2}$$

where $\alpha_c$ is the collection angle.

Subsequently, in order to calculate the binocular visual field relative to the animals body instead of relative to its head, we used the same formula for $v_{jk}$, but applied it in a body-centered reference system in which the z-axis is perpendicular to the platform or track, the x-axis is the instantaneous 'forward head axis' (see section 'head and eye coordinate systems') minus its projection in the z-axis and the y-axis is found as the cross product of the x and z axes.

Error Analysis—Propagation of Artificial Noise

To examine the dependence of our findings on the accuracy of our tracking systems, we re-tested several key results while adding Gaussian noise of varying standard deviation a $\sigma_{err}$ to the detected eye position angles.

The finding that eye movement velocities were greater for periods of free movement than for periods of head fixation was extremely robust with respect to potential errors in eye angle. The reported median absolute velocity remained significantly higher (P<0.05, n=10 rats) even for $\sigma_{err}=90°$. To test whether the observed differences could arise from errors that occurred only during free movement, we also compared uncorrupted observations during free movements to observations from head-fixation with added noise. In this case, the difference still remained significant for $\sigma_{err}$ up to 72°.

We next examined the finding that horizontal eye movements were positive correlated during head fixation and negatively correlated during free movement. This difference remained significant (P<0.05) for a, up to 50°, whether noise was applied to both head-fixed and freely moving periods or only to freely moving periods. The finding that correlation of vertical eye movements was less than zero during free movement persisted for $\sigma_{err}$ up to 40°.

We next examined the finding that both horizontal and vertical left-right differences of eye position were more variable in freely moving than in head-fixed animals. This finding remained significant for $\sigma_{err}$ up to 60° when noise was applied either to all data or only to data acquired during freely movement.

We next examined the findings that eye elevation and horizon angle showed greater variability when eye position was fixed to a reference position than when the observed eye positions were included. The difference in elevation variability remained significant for $\sigma_{err}$ up to 23°, while the difference in horizon angle variability remained significant for $\sigma_{err}$ up to 15°.

We next examined the finding that points on the eyeball surface that were initially aligned to the same target diverged over time and did not continue to track the same target point (FIG. 18). Here we sought to determine the level of tracking error that would be required to produce the observed divergences if the two eyeball surface points always targeted the same point in space. That is, we considered the case where both points tracked the same moving target through the environment, with noise corrupting the convergence to a single target. To carry out this test we used the same data as in FIG. 18. We used the target of the left eye, and adjusted the right eye's movements so that the same targets would occur for both eyes. We then converted the target direction vector into a pair of angles (both vertical and horizontal for the right eye), according to the relation $[v_1\ v_2\ v_3]=[\cos(\psi)\cos(\theta)\ \sin(\psi)\cos(\theta)\ \sin(\theta)]$. We then added Gaussian noise to $\psi$ and $\theta$ with standard deviation $\sigma_{err}$ and observed the root-mean-square distance between the two eyes' targets. For the original data observed in freely moving rats this distance was 18.7 cm. In order to observe a distance between targets at least this large for simulated data, it was necessary to set $\sigma_{err}$ to at least 15°.

Further advantageous embodiments will become evident from the attached drawings, detailed embodiments and results outlined below. In particular a summary of possible key features of the mobile camera system, the hardware (miniature camera), the hardware (animal tracking), software as well as concrete results thereto are given in the following detailed description, wherein

The following figures show detailed results of the methodology disclosed by and in connection of the FIGS. 1 to 14.

Figure 15:
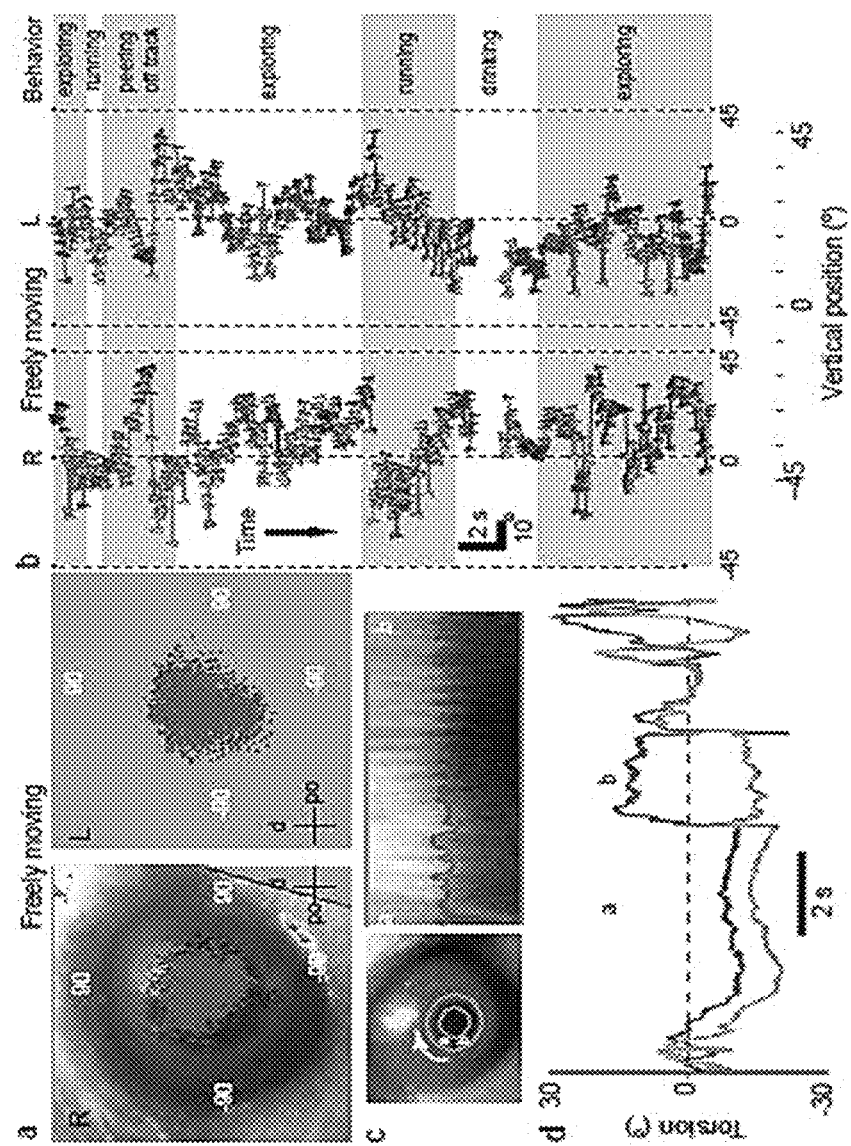
Figure 16:
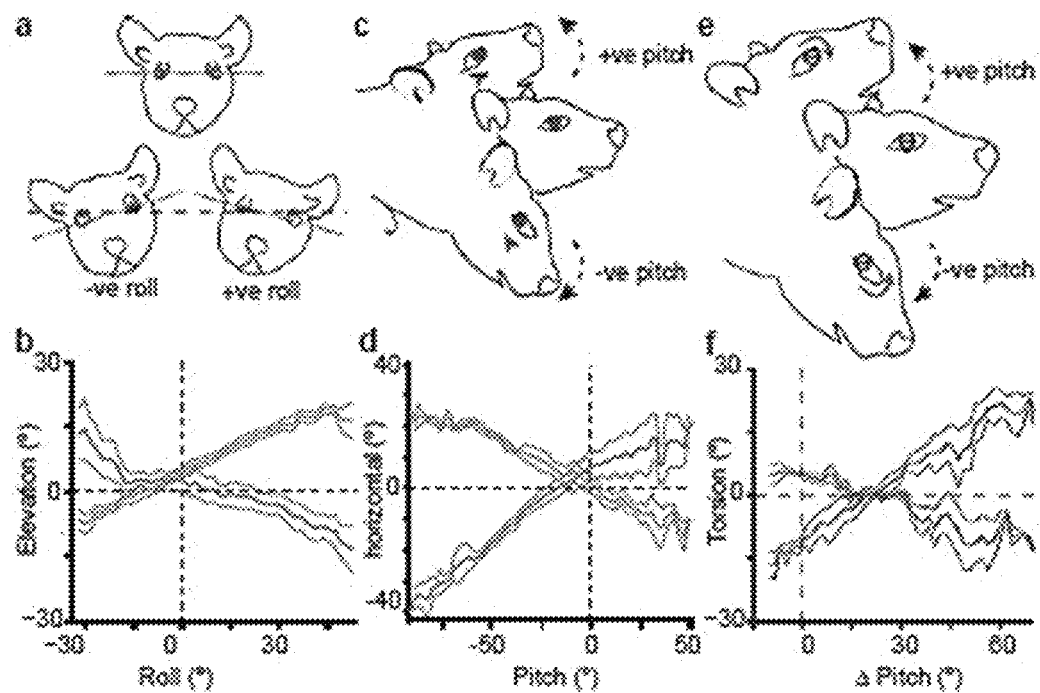
Figure 17:
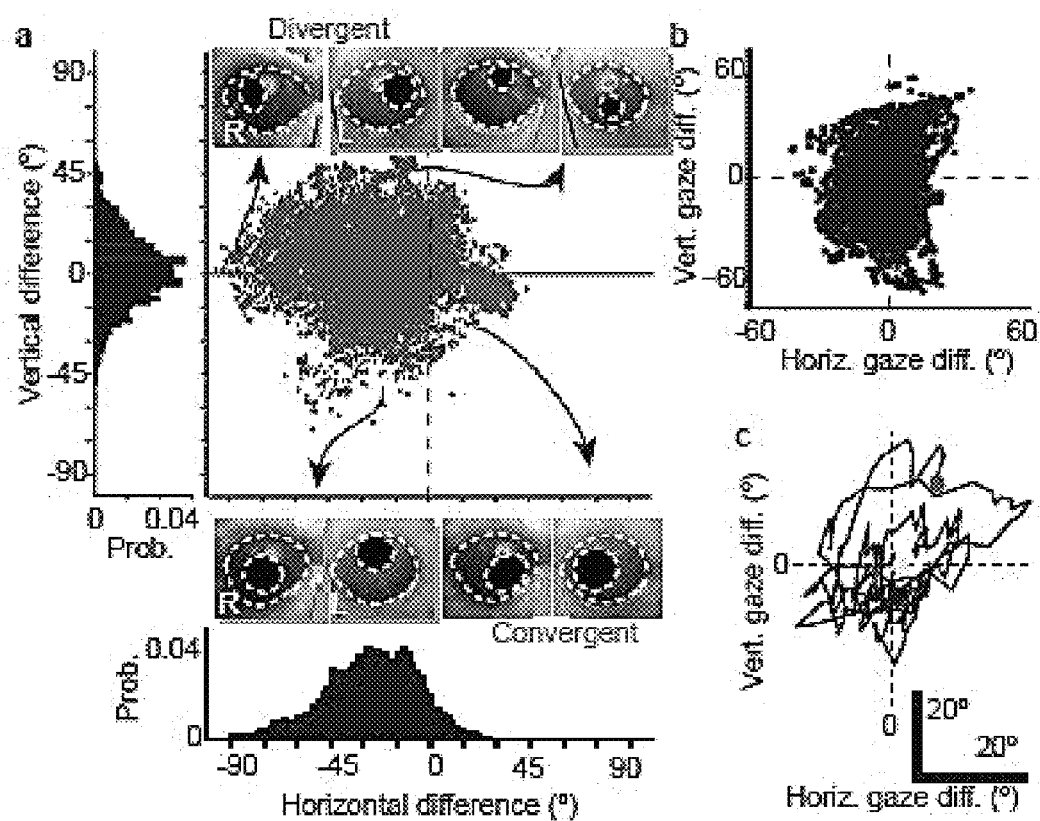
Figure 18:
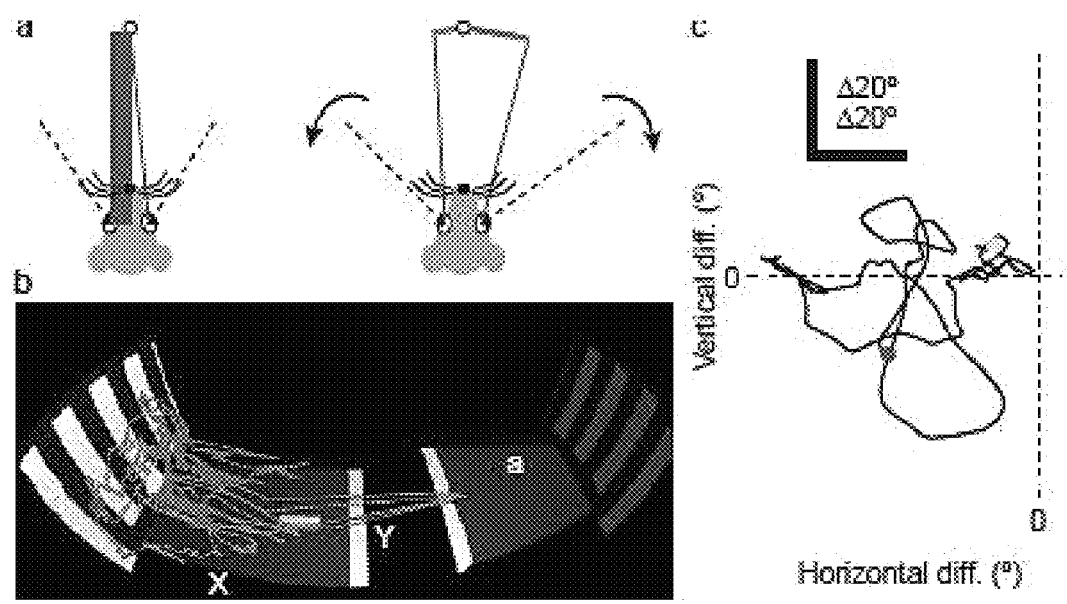
Figure 19:
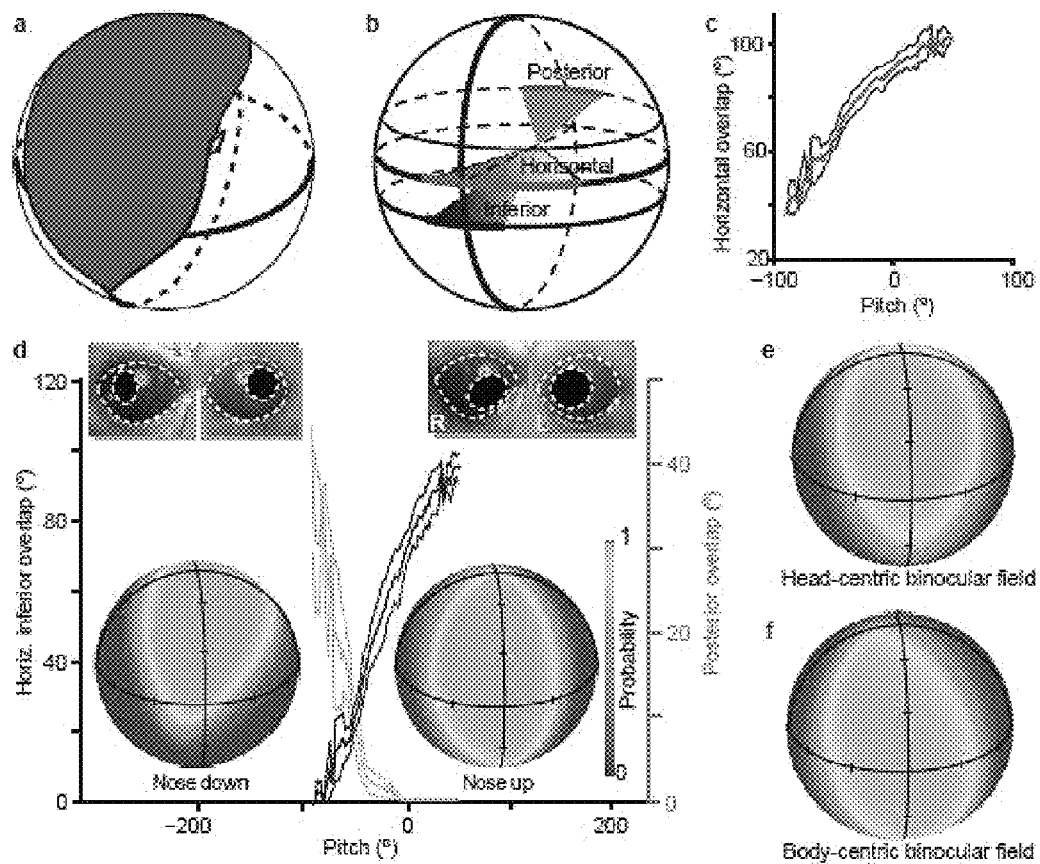

FIG. 15 shows eye movements in freely exploring rats;

FIG. 16 shows that eye movements are dictated by head movement and position in freely moving animals;

FIG. 17 shows asymmetrical eye movements in freely moving rats;

FIG. 18 shows eye movements in freely moving animals are not consistent with those needed for binocular fusion; and FIG. 19 shows overhead binocular overlap.

Figure 20:
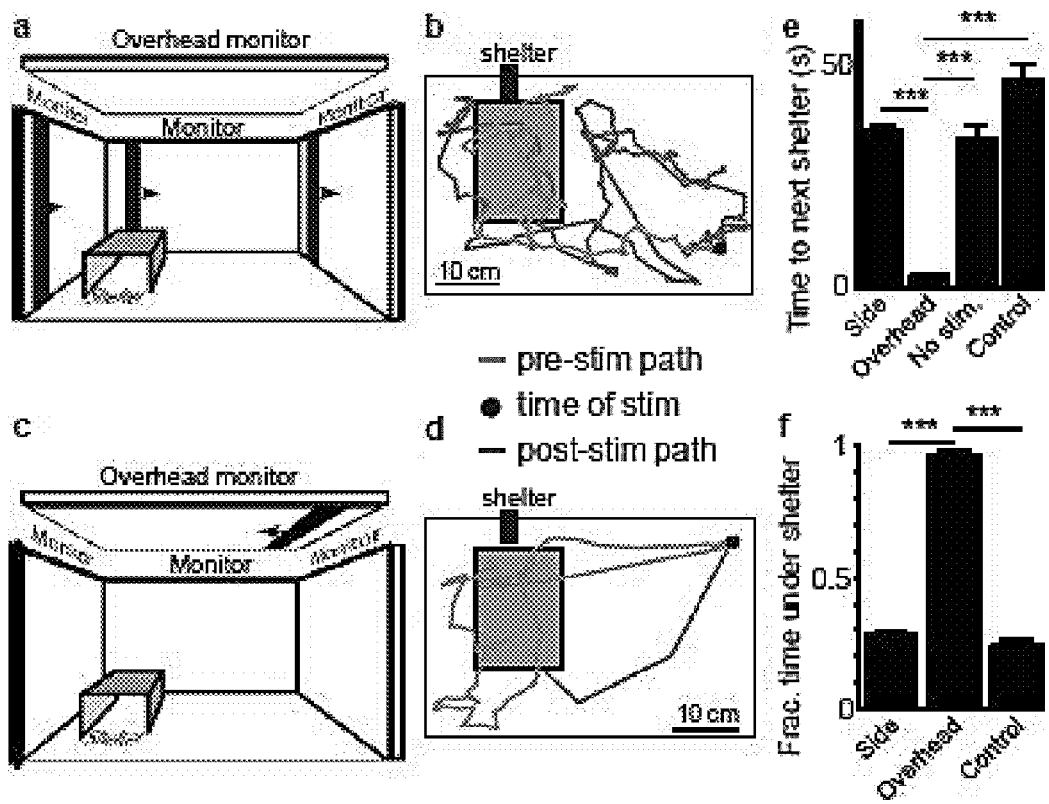

FIG. 20 shows shapes moving overhead selectively evoke shelter-seeking behaviour.

The following figures show, inter alia, in detail a miniaturized ocular videography system according to the present invention.

Figure 21:
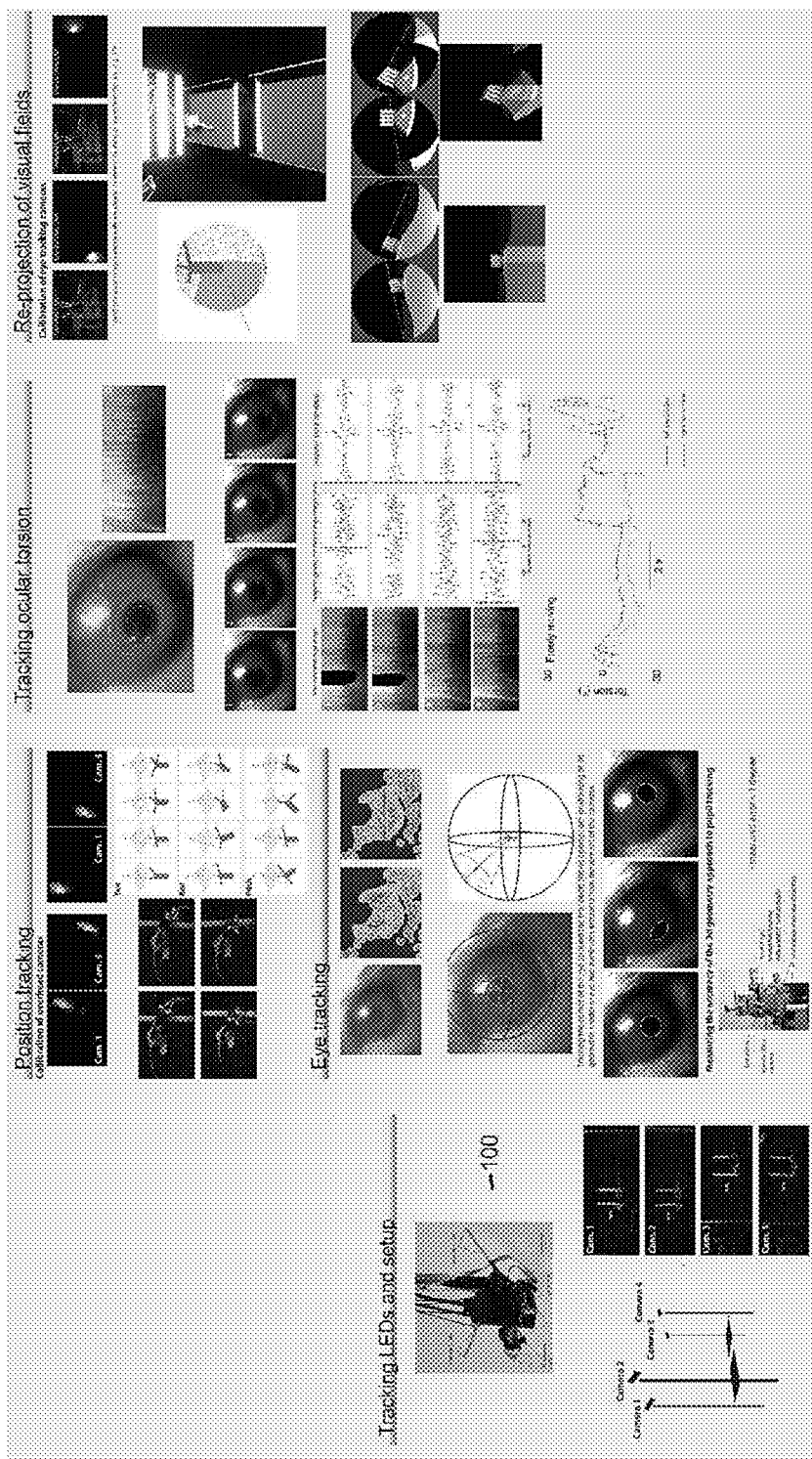
Figure 22:
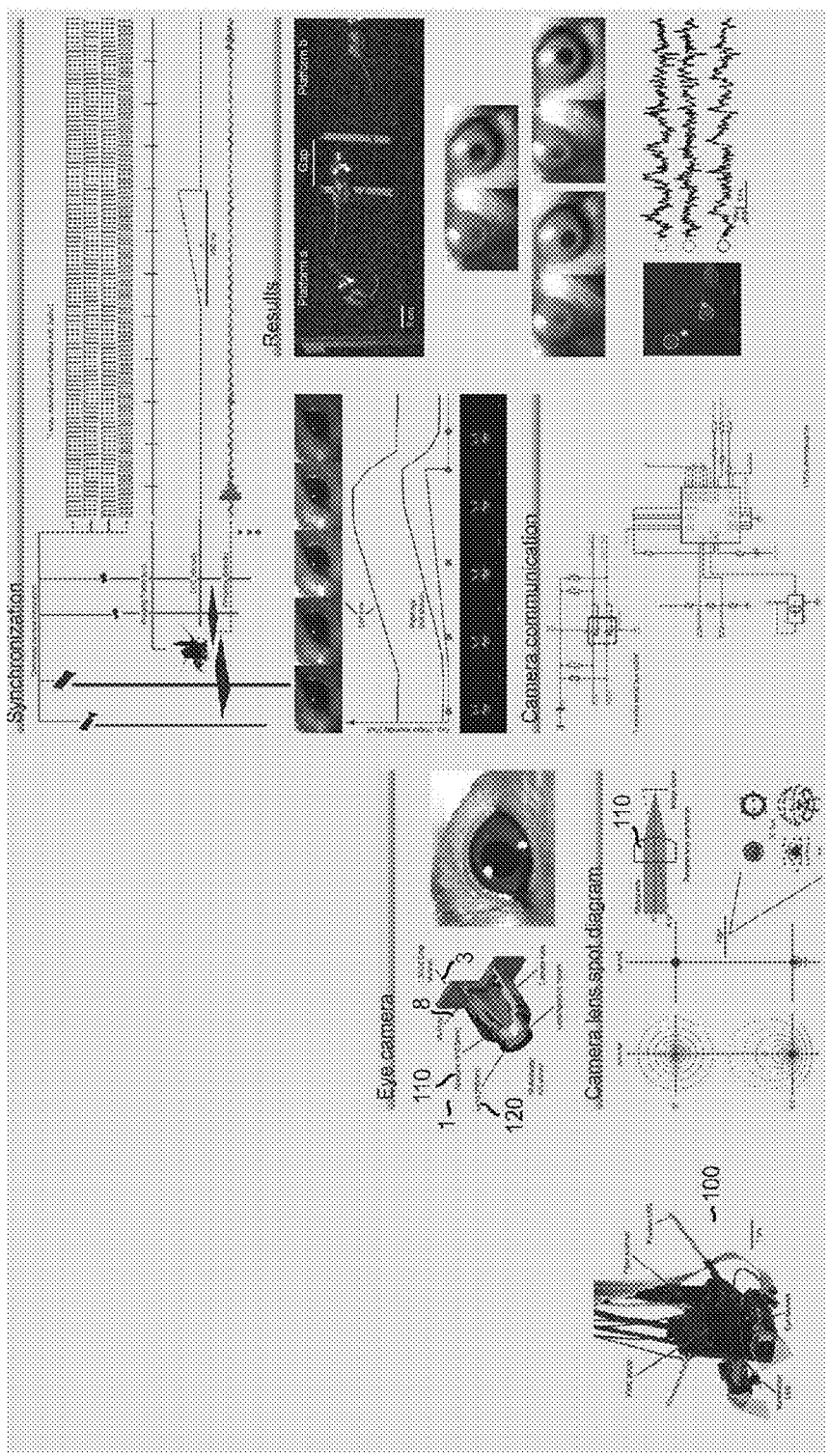

FIG. 21 shows the miniaturized ocular videography system and a summary of the key features of the overhead position tracking system and detection software methodology and capabilities, and FIG. 22 shows a schematic of the miniaturized cameras and camera communication electronics for eye tracking and a summary of the synchronization methodology employed by the system.

DETAILED DESCRIPTION OF THE INVENTION

Figure 1:
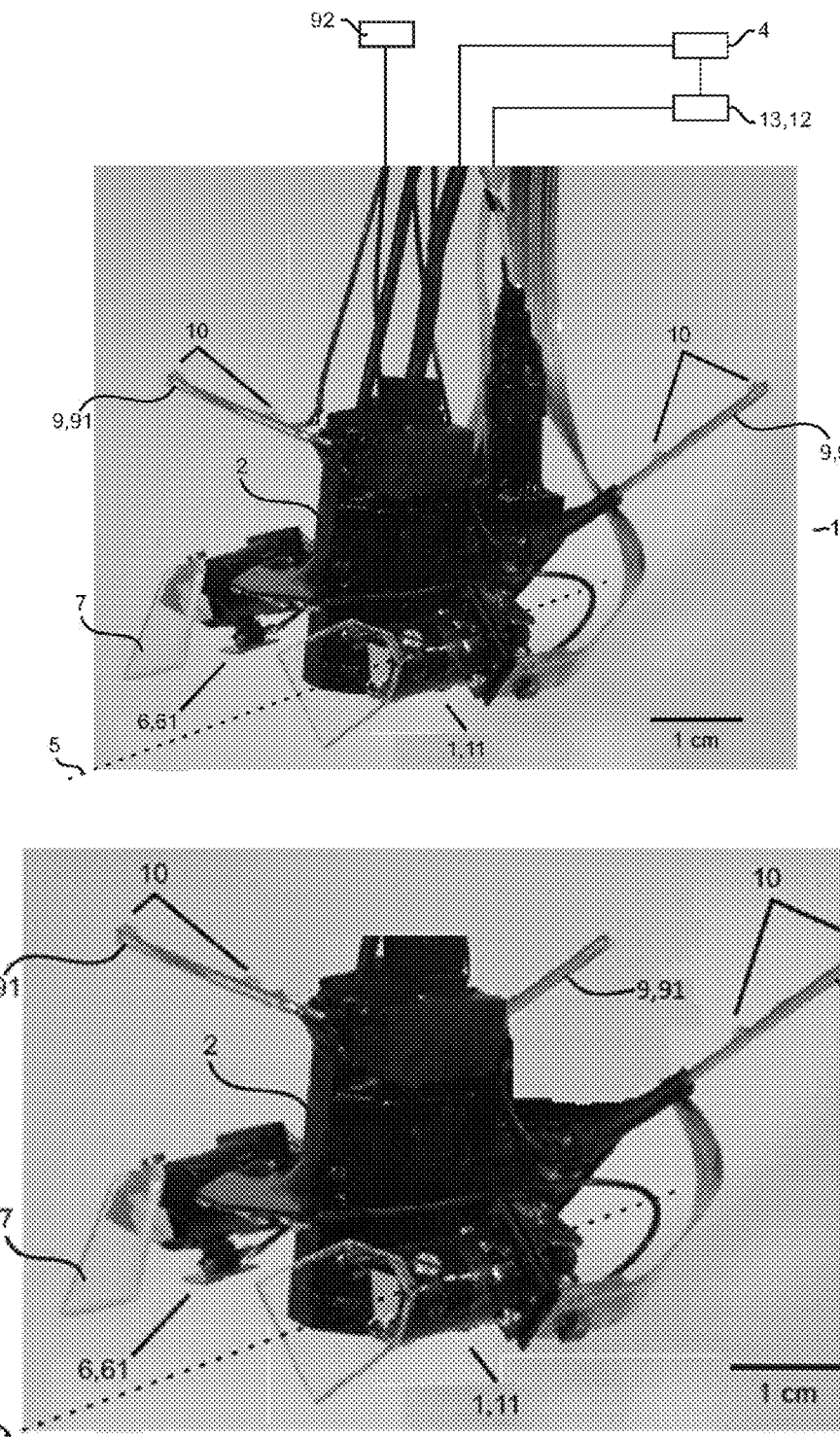
FIG. 1 shows in a schematic, perspective view an example of a ocular videography system according to one embodiment of the present invention.

FIG. 1 shows in a schematic, perspective view an example of ocular videography system 100 according to one embodiment of the present invention. In particular the miniature tethered mobile camera system 1 shown in FIG. 1 is small and light enough to be carried by small rodents (mice and rats). Additionally it can be used for oculo-videography (recording eye movements) in a freely moving animal, but could also be used for other applications. Camera development included development of software to operate and record data from the camera.

In particular the Ocular Videography System 100 for tracking an eye movement of an animal, in particular rats, comprises the camera system 1 suitable of being positioned on a head of an animal to track an eye movement of at least one eye of the animal, and a head mount 2 on which the camera system 1 is fixed or fixable.

Further the Ocular Videography System 100 comprises at least one image sensor 3 as well as at least one decoder 4, for decoding a signal detected by the image sensor 3, each being comprised by the camera system 1, wherein the camera system 1 is designed in such a way that it detects a movement of the eye and/or a movement of a head of the animal in a vertical and/or horizontal and/or a torsional direction to an optical axis 5 of the camera system 1 and/or of the optical axis of the animal's eye without interfering with the animal's natural motion dynamics.

In particular in FIG. 1 the two miniature cameras were mounted onto the light-weight plastic housing (=head mount 2) via mounting arms equipped with ball joints for flexible positioning of the cameras. Reflectors 7 (hot mirrors) (reflecting infrared (IR) but passing visible light) mounted on the end of the objective lens allow the cameras to be positioned to provide the best image of the eye while minimizing disturbance to the rat's visual field. IR light-emitting diodes (LEDs) were used for illumination of the eye. Three tracking arms (91) were also mounted on the housing 2, each bearing two IR LEDs used to track the position and orientation of the animal's head during the recording sessions. Note that the third tracking LED arm is obscured in this image by the cable bundle running off the top of the housing.

In summary within the Ocular Videography System 100 of the present FIG. 1 the camera system 1 is designed and mounted securely on the head mount 2 without interfering with the animal's field of view. The decoder 4 for decoding the signal detected by the image sensor is mounted off of the animal, wherein the camera system 1 comprises two light emitting elements 6 for guiding and emitting light towards the animal's eyes, and two light reflectors 7 for reflecting at least partially the light reflected from the animal's eye to the image sensor/s 3 of the camera system 1, wherein the camera system 1 is mounted on the head mount 2 outside of the visual field of the animal's eye.

The light emitting element 6 is arranged within the camera system 1 such that it illuminates the animal's eye off-axis to the optical axis 5 of the animal's eye and each of the light emitting element 6 is a light emitting diode 61 (LED) emitting light at least in the infrared optical spectrum, wherein the reflector 7 transmits at least partially light in the visible spectrum and reflects light in the infrared spectrum of light.

The IR-transmission filter 8 being comprised by the camera system 1, wherein said IR-transmission filter 8 is arranged in an optical path of the light emitted by the light emitting element 6 and prevents the superimposition of light in the visible optical spectrum with the light emitted by said light emitting element 6.

The head position tracking system 9 is designed to track a position of the animal's head within a predefined, stationary coordinate system originating outside the animals body, wherein said head position tracking system 9 comprises three tracking arms 91 mounted on the head mount 2 in a predefined position to each other, wherein on each of the tracking arms 91 one or more light emitting elements 10, in particular light emitting diodes (LEDs), being different to the light emitting element 6 for guiding light in the animal's eye, are mounted, and the head position tracking system 9 further comprises a head movement detection device 92 mounted off of the animal's body and stationary within the coordinate system, wherein the head movement detection device 92 detects detects a movement of the light emitting elements 10 and is designed to calculate a position of the animal's head according to the position and/or the movement of the light emitting elements 10.

Additionally, the camera system 1 comprises a lens unit 11 for guiding light at least partially emitted by the camera system's 1 light emitting element 6 into the image sensor 3 of the camera system 1.

In the present embodiment it is important to note that the lens unit 11 comprises at least one plano-convex lens 120 being arranged in a reverse orientation, and an aperture 110 of at least 0.02 mm to at most 1.2 mm, preferably at least 0.3 mm to at most 0.5 mm, wherein the lens unit 11 is glued to the camera chip 3.

A core engine 13 is implemented within a processor 12 of the camera system 1 controlling measurement parameters of the camera system 1 and capable of streaming data onto one or several hard drives, wherein the core engine 13 is capable of processing independent eye movements of both eyes of the animal.

Below, a summary of the detailed measurements are given, wherein for simplicity reasons same or similar acting features are corresponding to the same reference numeral as given above.

The key technical advances of the ocular videography system shown in FIG. 1 are:
- design and assembly of suitable small and light camera optics for providing high contrast and large depth of field
- design of suitable small and light on-board electronics for camera control and data transfer
- communication and data transfer over cables light enough to be easily carried by the animal but still suitable for the electronic purpose.
- design and manufacture of a suitable reflector element to allow positioning of the camera in a way that minimizes disturbance to the animals field of view
- design, manufacture and assembly of a suitable (small and light) mounting arm system for mounting the cameras onto the animals head while still allowing flexibility of camera positioning for adjustment of the field of view
- onboard infrared illumination which is not visible to the animal, and allows data acquisition in a broad range of ambient lighting conditions (darkness to bright lighting)
- Precise animal motion detection (3-dimensions) using 6 head-attached IR-LEDS (2 LEDs on 3 arms) recorded by external cameras.

In particular, the optics comprised within the ocular videography system of FIG. 1 comprises at least one of the following technical features or combinations thereof:
- Single plano-convex lens in reverse orientation with an 0.5 mm aperture directly following the convex lens (therefore on the primary plane of the lens)
- Infrared filter (RG780) near the camera chip inside the objective tubing
- The lens unit is glued after adjustment to save weight
- Lens unit carries an infrared reflector transparent to visible light to reduce visual field obstruction for the animal
- Image plane is illuminated by a single IR-LED (Osram SFH4050, 850 nm) far off-axis to avoid reflections off the eye near the pupil
- body for the optics and mounts for IR-reflector and IR LED for illumination custom produced in-house, and assembly of optical components done by hand In particular the electronics comprised within the ocular videography system comprises at least one of the following technical features or combinations thereof:
- The camera chip is an Aptina MT9V024 which supports WVGA (752×480 pixels), max. 60 fps, supports LVDS data transmission, controlled via SPI ($I^2C$ compatible)
- Camera chip mounted on a custom-designed printed circuit board with minimal electronics: voltage regulator, decoupling capacitors, oscillator (27 MHz), $I^2C$ bus repeater
- Cabling consists of isolated AWG42 cables:
  reset line
  supply voltage (double)
  ground (double)

data and clock line (SPI)

twisted-pair LVDS (without shield)

a standard deserializer (12 bit) to feed the parallel data into the computer interface board (development board, Aptina Demo 2X)

In particular the hardware (animal tracking) comprised within the ocular videography system comprises at least one of the following technical features or combinations thereof:

The animal carries 6 IR-LEDs (Osram SFH4050, 850 nm) on 3 arms mounted on the head mount Motion of the head is tracked using 4 high-speed GigE cameras (Basler AG, piA640-210 gm)

In particular the software comprised within the ocular videography system comprises at least one of the following technical features or combinations thereof:

The software consists of several parts which are combined to precisely track animal position as well as eye movement.

Video Capture:

Acquisition software has been developed to control camera parameters and record data from the camera, specifically suitable for the current application of imaging from freely moving animals. Acquisition software features include:

A core engine written in Visual C++ that controls camera hardware and efficiently streams data onto one or several hard drives.

A graphical user interface written in Matlab with user controls and an image display, which can send and receive data from the core engine.

Each attached camera can be uniquely identified by the acquisition software. Camera settings such as image size, exposure time, gain and frame rate are remembered for each camera when the software is started or the camera is reattached. Camera settings can be saved to a settings file for each type of experiment.

A custom lossless image format that can be easily read and manipulated in Matlab.

Calibration of Tracking System:

A software suite for calibration of the camera systems (head position and eye tracking) executable in Matlab has been developed.

Favourable is also the following taking the ocular videography system described above into account:

expansion of the systems capabilities by using alternative camera chips (eg. CMOSIS 300 fps);

untethered (wireless or optical) operation;

precise gaze direction estimation.

Figure 2:
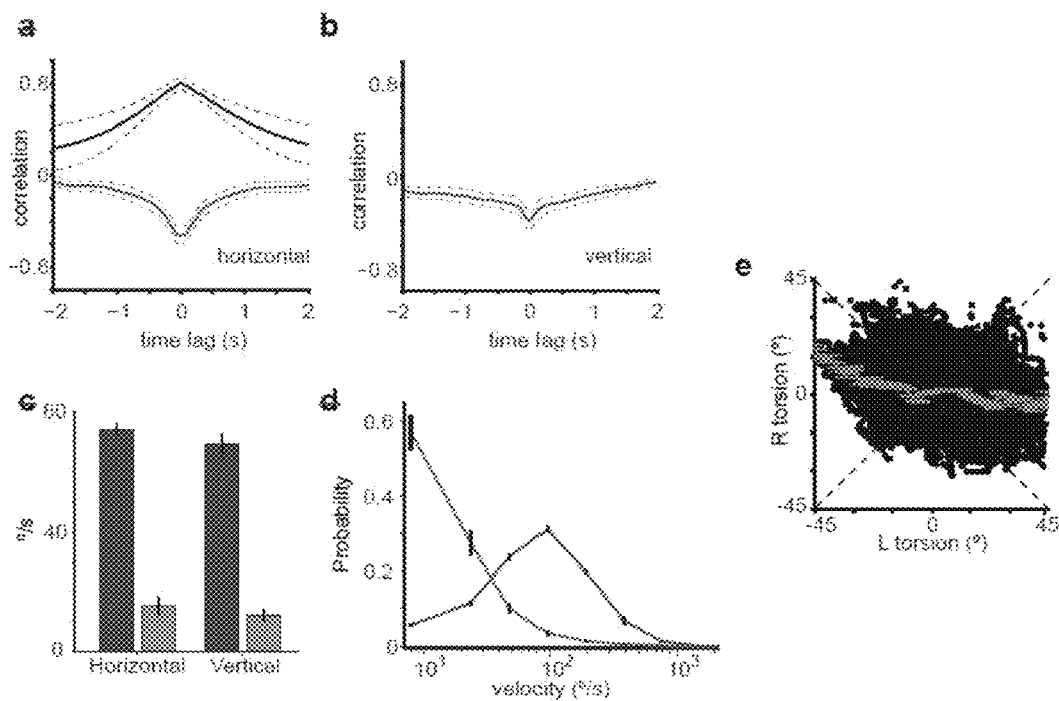
FIG. 2 shows additional characteristics of eye movements in freely moving and head-restrained animals.

FIG. 2 shows additional characteristics of eye movements in freely moving and head-restrained animals. In particular it shows a, plot of average cross-correlations between movements of the two eyes in the horizontal plane for freely moving (solid red) and head restrained (solid black) animals with standard error (dotted lines). Mean correlation coeff. at 0 lag for freely moving animals −0.5±0.1, n=7 datasets from 4 animals, and for head-restrained animals 0.8±0.1, n=5 datasets from 4 animals. b, average cross-correlations for vertical eye movements is given.

Mean correlation coeff. at 0 lag for freely moving animals −0.4±0.1, n=7 datasets from 4 animals. Plot conventions as in a. Note that head-restrained animals showed no vertical eye movements. c, Fraction of recording time in which vertical and horizontal eye movements were observed (blue, n=7 datasets from 4 animals) and head restrained animals (green, n=5 datasets from 4 animals). d, eye movement velocity distributions for freely moving (blue) and head restrained (green) datasets (datasets as for a). The average instantaneous velocity for both horizontal and vertical movement was significantly less than that observed in freely moving animals (p<0.001, rank sum tests). e, scatter plot of right against left eye torsion for one freely moving recording. Individual measurements shown as black points and average with S.E. shown in blue.

Figure 3:
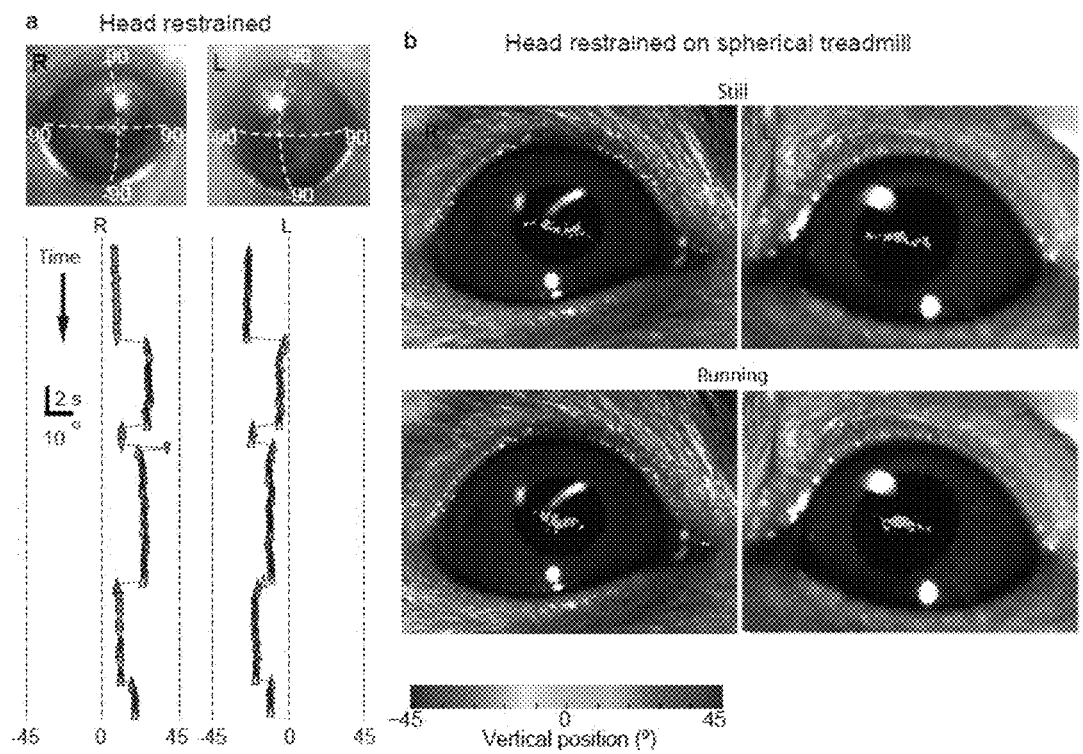
FIG. 3 shows left and right eye movements in head restrained rats.

FIG. 3 shows left and right eye movements in head restrained rats. a, eye images and pupil positions (upper) from head-restrained rat (~11,000 data points, same animal as in FIG. 15a and in b) and kinetics of eye movements (lower). Plot conventions for kinetics as in FIG. 15b. Orientation of eye images as in FIG. 15a. Colorscale for vertical movements under lower panel in b. b, eye movements in a head restrained rat on a spherical treadmill either still (upper) or running (lower). Eye movements were restricted to the horizontal plane in both cases. Green dots represent individual pupil position measurements.

Upper images of still rat contains 1066 position measurements, lower images of running rat contain 1053 measurements.

Figure 4:
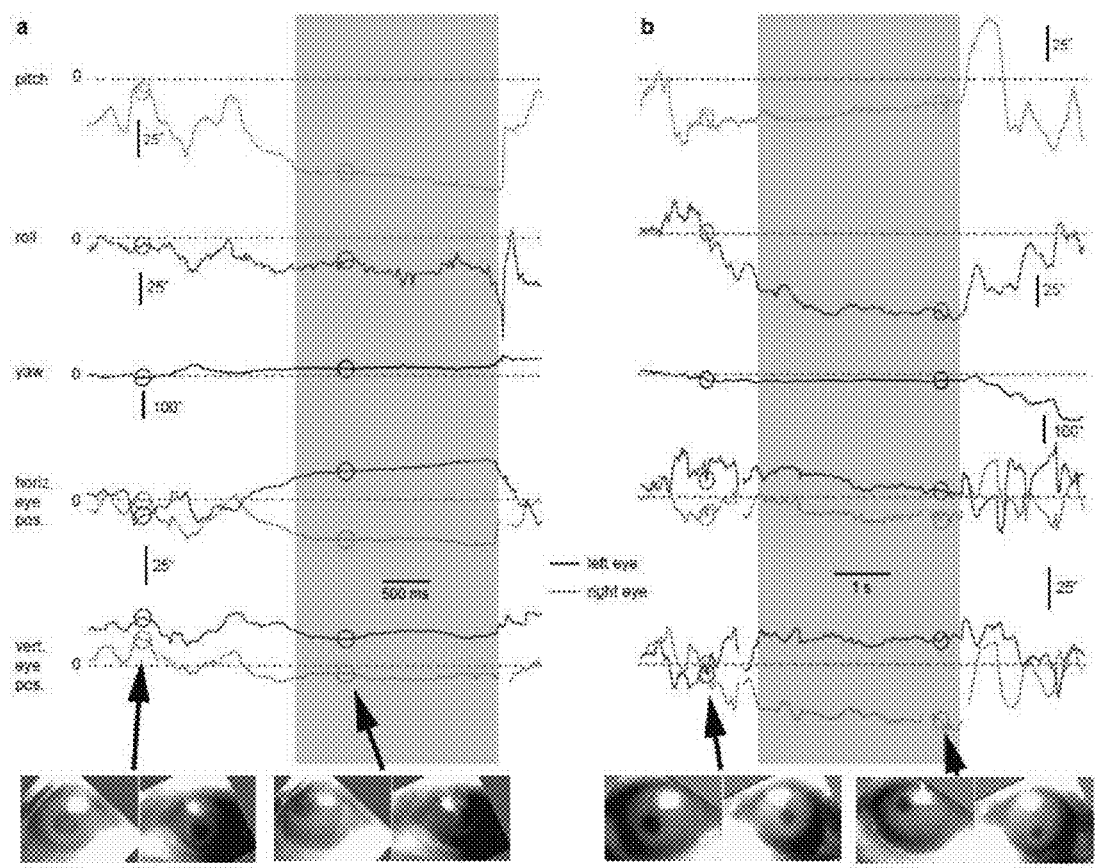
FIG. 4 shows eye positions resulting from pitch or roll of the head in freely moving rats are held as long as the pitch or roll is maintained.
Figure 5:
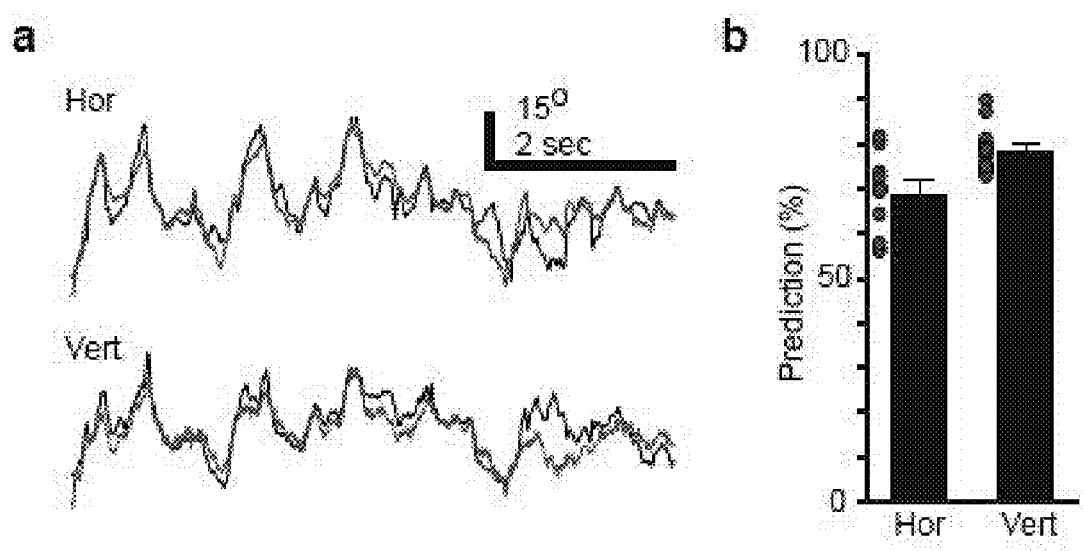
FIG. 5 shows a model of eye movements.

FIG. 4 shows eye positions resulting from pitch or roll of the head in freely moving rats are held as long as the pitch or roll is maintained. a, an example from one animal of the eye positions resulting from sustained, large amplitude pitch of the head. Gray box represents segment during which strong pitch is maintained. Note that both horizontal and vertical eye positions are maintained so long as the pitch and roll of the head remain constant. In this example, head pitch of >80° is maintained for a period of several seconds (animal was peering off the edge of the track towards the floor), and this resulted in a prolonged period of extreme divergence of the eyes in the horizontal plane. Note also that the maintained slight roll of the head during this period also results in sustained vertical eye positions consistent with the observed roll. The brief periods of discontinuity in the eye position traces represent periods where eye tracking was not possible (closure of the eye). b, example of eye positions resulting from sustained roll of the head. Note here also that sustained roll results in sustained divergence in the vertical plane, and that the simultaneous FIG. 5 shows a model of eye movements. a, example data segment from one freely moving animal showing measured (black) and predicted (red) horizontal (upper) and vertical (lower) positions of one eye. The predictive model used head pitch and roll to predict eye positions. b, models average prediction of both vertical and horizontal pupil position for 4 animals. Filled circles represent individual recording sessions. Average vertical variance reduction 78±2% (n=3 animals), and average horizontal variance reduction 69±3% (n=3 animals).

Figure 6:
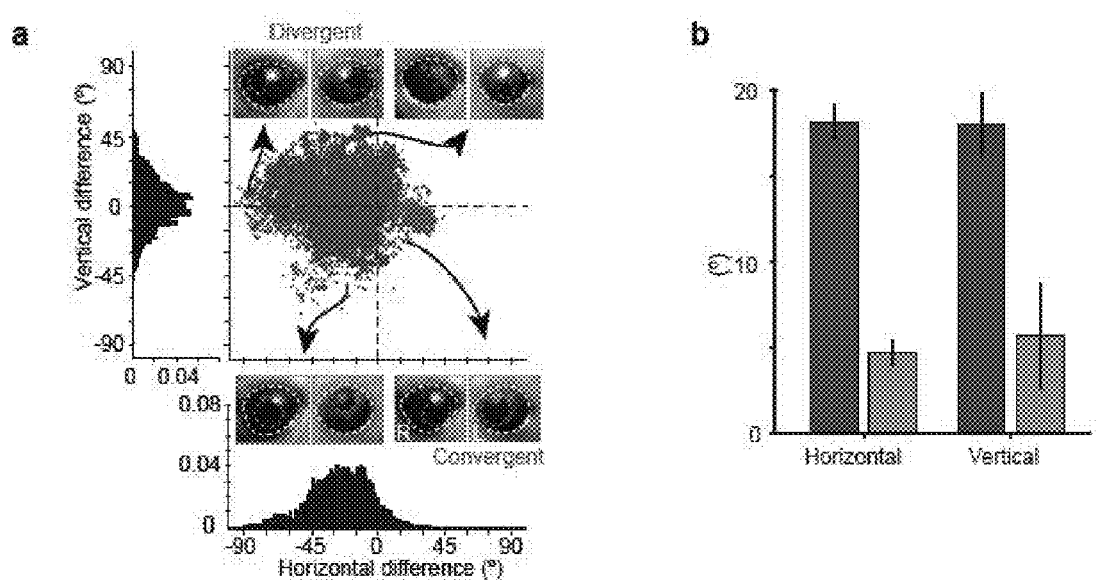
FIG. 6 shows ocular misalignment in freely moving rats.

FIG. 6 shows an ocular misalignment in freely moving rats. a, distributions of the difference between left and right eye positions for a freely moving (blue) and headrestrained (red) rat. Each point represents the right eye position minus the left eye position for a single frame. Increasing positive x values represent convergence of the eyes, while increasing negative x values represent divergence. Increasing negative y values represent a ventral shift of the right eye and dorsal shift of the left eye, and vice versa for increasing positive y values. The histograms beside x and y axes show the distribution of values presented in the plot. Inserts show example image pairs from four positions within the distribution (arrows). Conventions for presentation of eye images in inserts as in FIG. 15a. b, average standard deviation of horizontal and vertical eye position differences for freely moving (blue, 7 datasets from 4 animals) and head-restrained (green, 5 datasets from 4 animals) rats.

Figure 7:
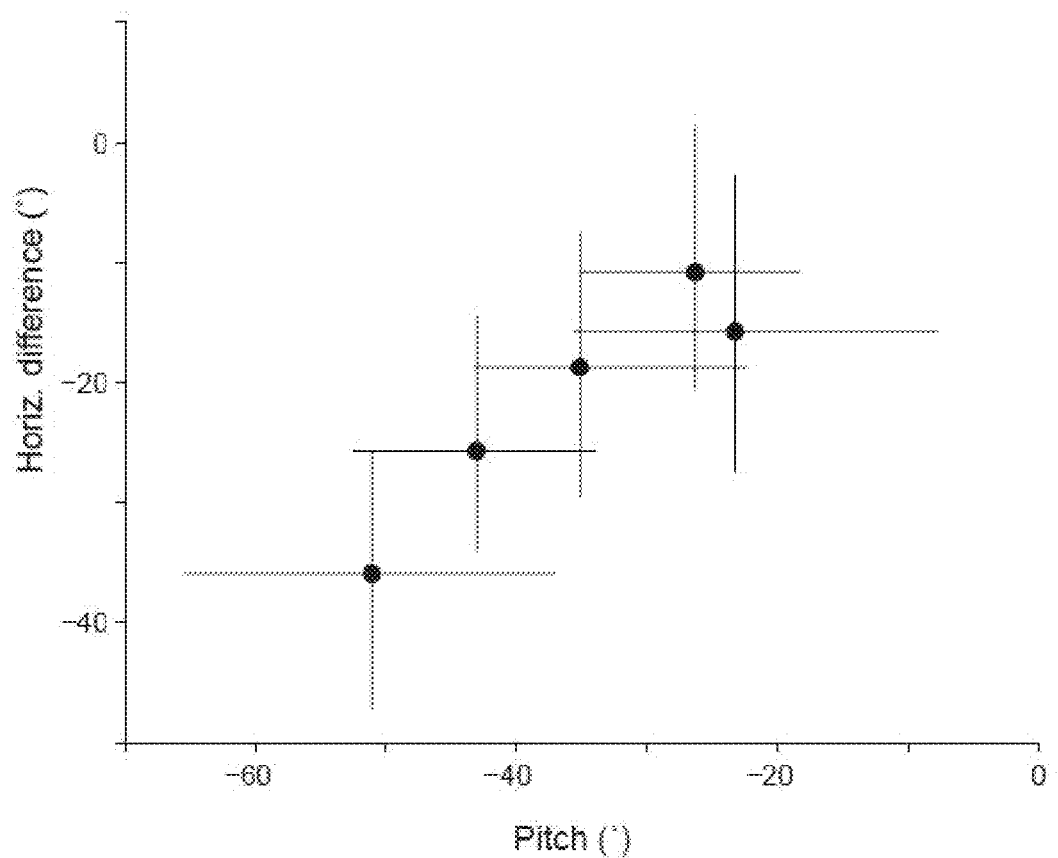
FIG. 7 shows a relation between preferred head pitch during free movement and difference in horizontal pupil position.

FIG. 7 shows a relation between preferred head pitch during free movement and difference in horizontal pupil position. Median and quartile range of the difference in horizontal pupil position (right-left pupil position) for 5 animals. Each animal had a slightly different preferred head posture while performing the task. Consistent with the relationship between head pitch and horizontal eye position mediated through the vestibulo-ocular reflex, this resulted in a predictable difference in the median difference in horizontal pupil position.

Figure 8:
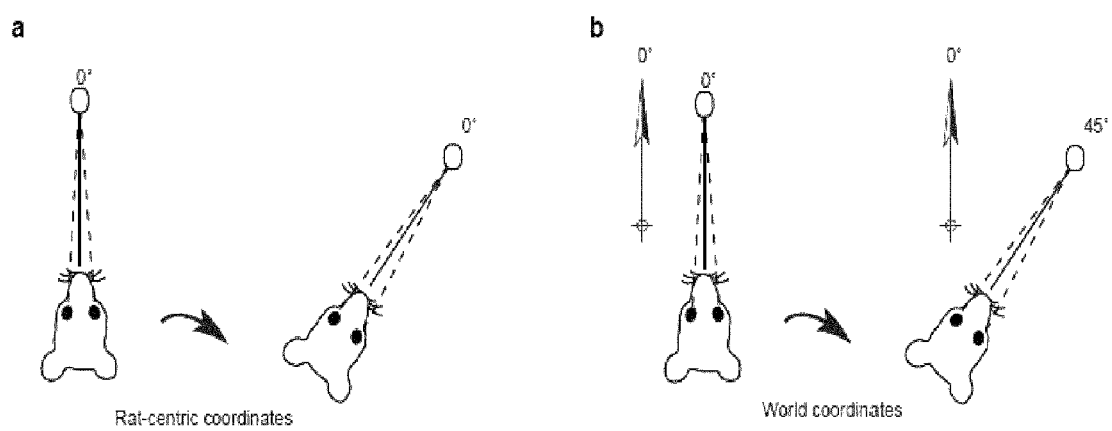
FIG. 8 shows Rat-centric versus world-centric coordinate systems.

FIG. 8 shows a Rat-centric versus world-centric coordinate systems. a, ratcentric coordinates in which the bearings to objects around the animal are given relative to the rats nose. b, world coordinates, in which the zero degree reference remains fixed relative to the movements of the animal.

Figure 9:
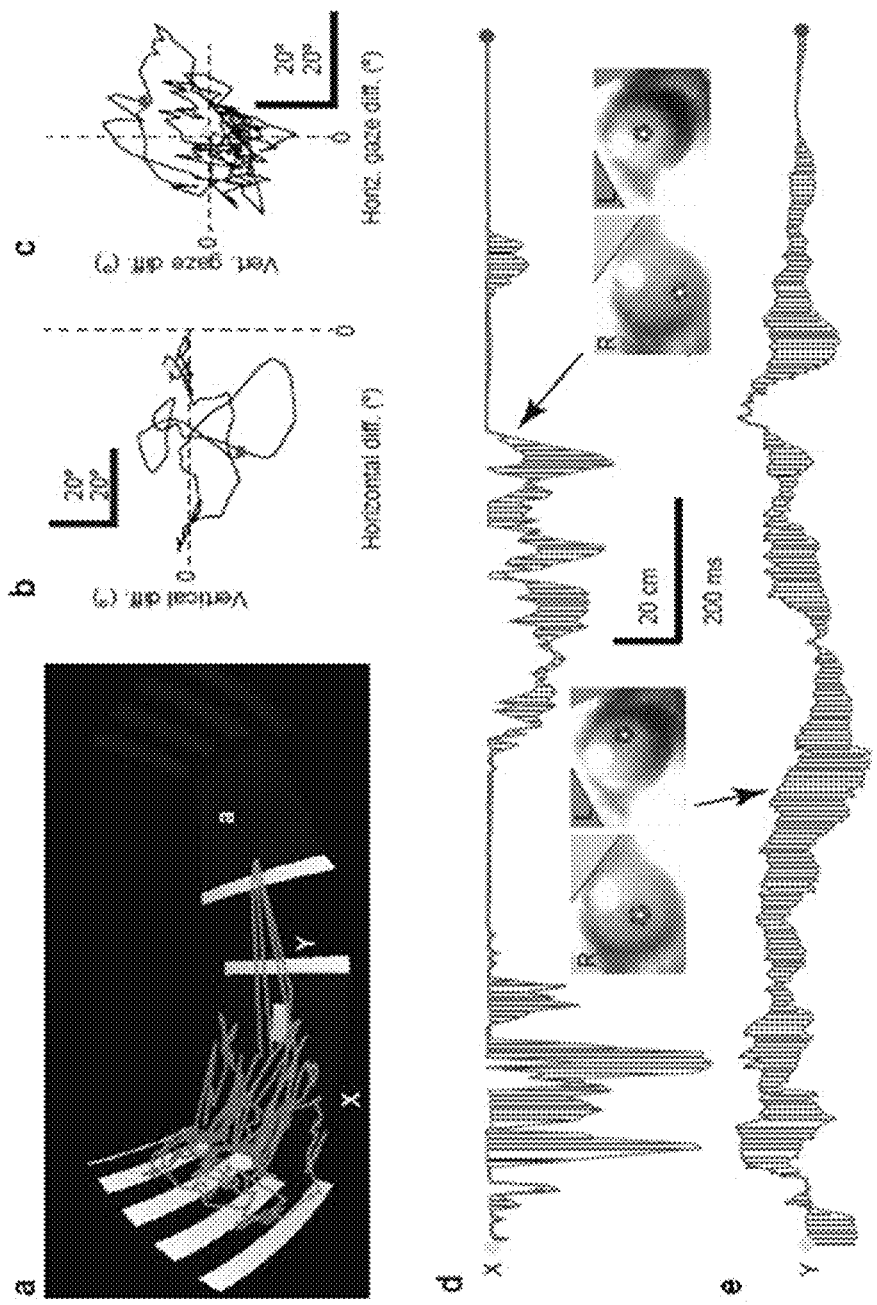
FIG. 9 shows ocular misalignment during a single gap cross.

FIG. 9 shows ocular misalignment during a single gap cross. a, rendering of jumping arena used in experiments showing monitors (far left and right stripes), initial animal position (a), initial gaze position (yellow dot for each eye) and subsequent gaze positions of the two eyes (right, green and left, blue lines) as the animal jumps the gap (end gaze positions shown as red dots). b, plot of the difference between left and right eye positions for the data shown in a (same convention as FIG. 17a) starting with yellow dot and ending with red dot 1.7 s later with all consecutive time points joined (black line). c, plot of the difference in left and right eye gaze vectors for the same data as in a with the starting (yellow dot) and finishing position (red dot) denoted. d, relative position of both left (blue) and right (green) eye gaze as it intersects the jumping track for the x-axis through time, with each time point denoted (black lines) as well as start (yellow dot) and finish (red dot). The same data as in a-c. e, relative position of both left (blue) and right (green) eye gaze as it intersects the jumping track for the y-axis, with each time point denoted (black lines) as well as start (yellow dot) and finish (red dot). The same data as in a-d. Inserts show examples of eye positions at the times indicated by the arrows.

Figure 10:
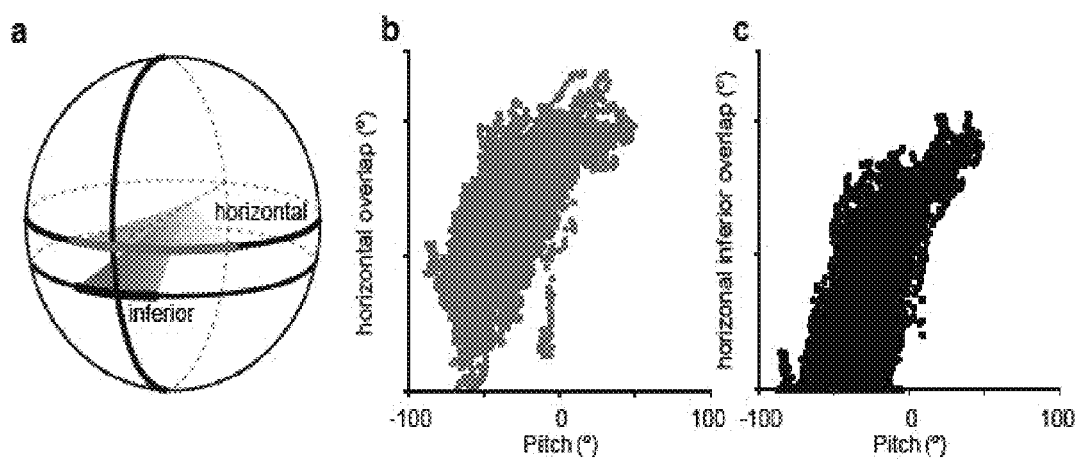
FIG. 10 shows individual example of the effect of changing pitch on the measured width of the binocular visual field at two locations around the head.

FIG. 10 shows individual example of the effect of changing pitch on the measured width of the binocular visual field at two locations around the head. a, schematic showing the locations in which the width of the binocular field was measured. b, binocular field width in the horizontal location as a function of head pitch. c, binocular field width in the horizontal inferior location as a function of head pitch.

Figure 11:
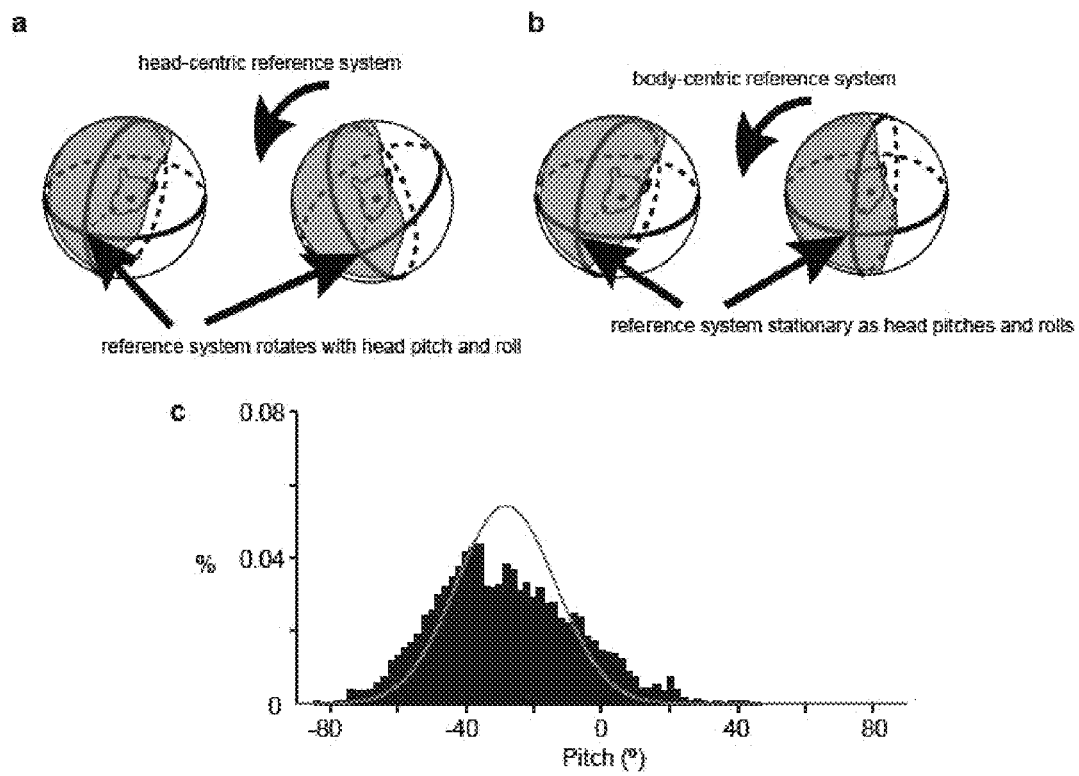
FIG. 11 shows schematic of the head-centric and body-centric reference systems used for calculation of the mean location of the binocular visual field during free movement.

FIG. 11 shows schematic of the head-centric and body-centric reference systems used for calculation of the mean location of the binocular visual field during free movement. a, head-centric reference system. The orientation of the reference system remains aligned in all planes with the animal's head during head movements, with the origin of the system being directly in-front of the nose. b, body-centric reference system. The origin of the reference system remains in-front of the animal's nose, meaning that it turns in the x-y plane with the turning (yaw) of the animal's head. However, the horizontal plane remains fixed and horizontal, and the vertical plane remains locked with the horizontal plane, so that the pitch and roll of the animals head repositions the binocular field within the reference system. c, distribution of head pitch angles recorded for the freely moving rat.

Figure 12:
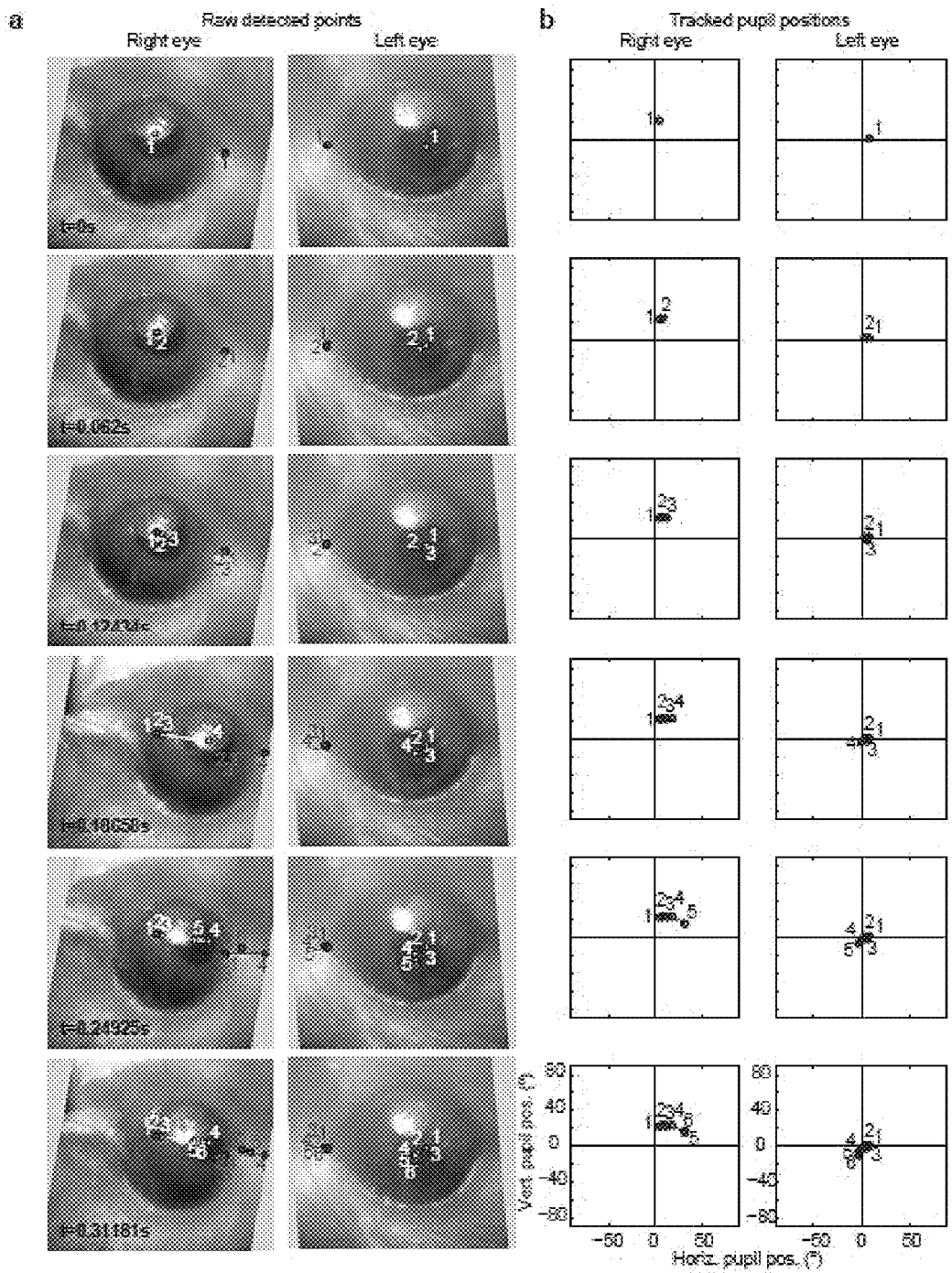
FIG. 12 shows elimination of artifacts due to camera movement by tracking of the corner of the eye.

FIG. 12 shows elimination of artifacts due to camera movement by tracking of the corner of the eye. a, series of six image pairs from one freely moving animal. The animal bumped the camera over the right eye into the edge of the track between the third and fourth images in the sequence, resulting in a considerable sideways displacement of the right eye in the subsequent image. The tracked eye corner positions are shown in red in each image, and the tracked pupil center position shown in white. Eye corner and pupil center positions from all preceding images in the sequence are shown with correspondingly numbered circles. Time relative to the first image pair in the sequence is shown in the bottom left corner of each right eye image. b, Tracked pupil positions for the right and left eyes obtained from the corresponding image pairs in a. Note that the effect of the large movement of the camera occurring just prior to the fourth image pair in the sequence is entirely eliminated by the simultaneous tracking of the corner of the eye.

Figure 13:
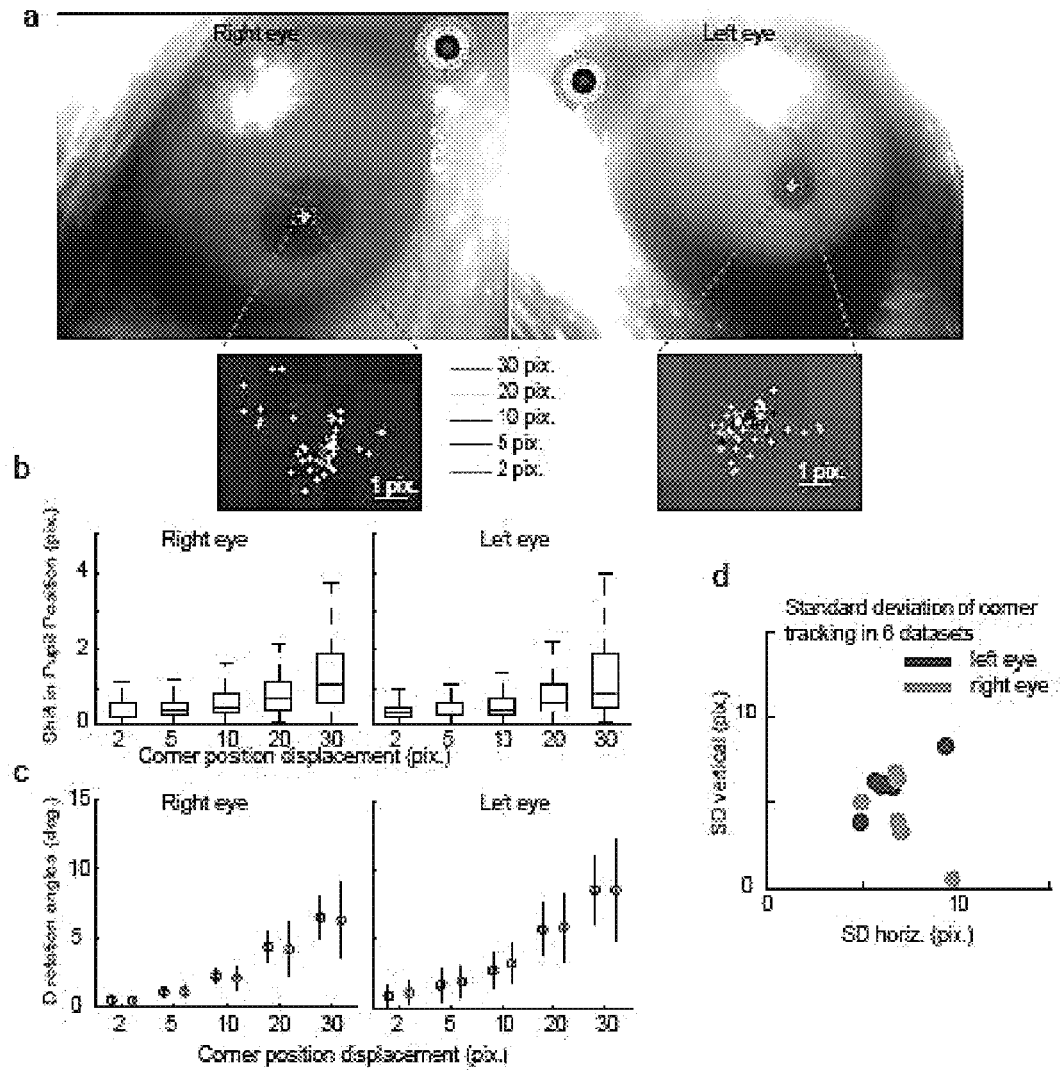
FIG. 13 shows effect of displacement of the detected eye corner position on tracked pupil position.

FIG. 13 shows effect of displacement of the detected eye corner position on tracked pupil position. a, example images of right and left eyes from one animal showing originally detected eye corner position (dark blue solid circle) and the displaced corner positions (open circles) used for assessing the sensitivity of pupil tracking to errors in corner tracking. The corner position was displaced by 2, 5, 10, 20 and 30 pixels (green, red, black, yellow and cyan open circles respectively) at 20 different angles, and the resulting effect on the tracked pupil position assessed. Tracked pupil positions resulting from the displaced corner positions are plotted as crosses on each eye image (color matching the amplitude of corner position displacement), with an enlargement of the center of the pupil (red dashed square) shown underneath. Note that errors in both the tracked location of the pupil in the image (shown in b) and in the measured eye position (shown in c) caused by erroneous corner tracking are very minimal even for displacements of 20 or 30 pixels, which would have been detected during verification procedure implemented in the analysis. b, boxplots of pooled data from 3 animals showing for left and right eyes the distribution of displacements of the tracked pupil location in the image resulting from displacements of the detected corner position. The displacement of the pupil location was calculated as the Euclidean distance between the pupil location originally returned by the algorithm and that returned after displacement of the corner position. Boxplots show median (red) and 25th to 75th percentile as box edges. Data were taken from 10 randomly-selected image frames from datasets from 3 different animals, with pupil positions calculated for each frame after displacement of the corner position by each of the range of radii and angles described above. c, plots showing mean difference in horizontal (black) and vertical (red) angular rotation of the eye resulting from displacement of the corner position. Mean difference from originally tracked rotation angles are shown for the same data as shown in b. Error bars represent standard deviation. d, plot showing standard deviation of tracked medial corner (tear duct) positions for left (blue) and right (green) eyes from 6 animals. Standard deviations were calculated for all marked frames, including frames where there was an actual movement of the eye, and are therefore an overestimate of any error in tracking of the eye corner. This can, however, be used as an upper bound for the frame to frame variation in marked corner position.

Figure 14:
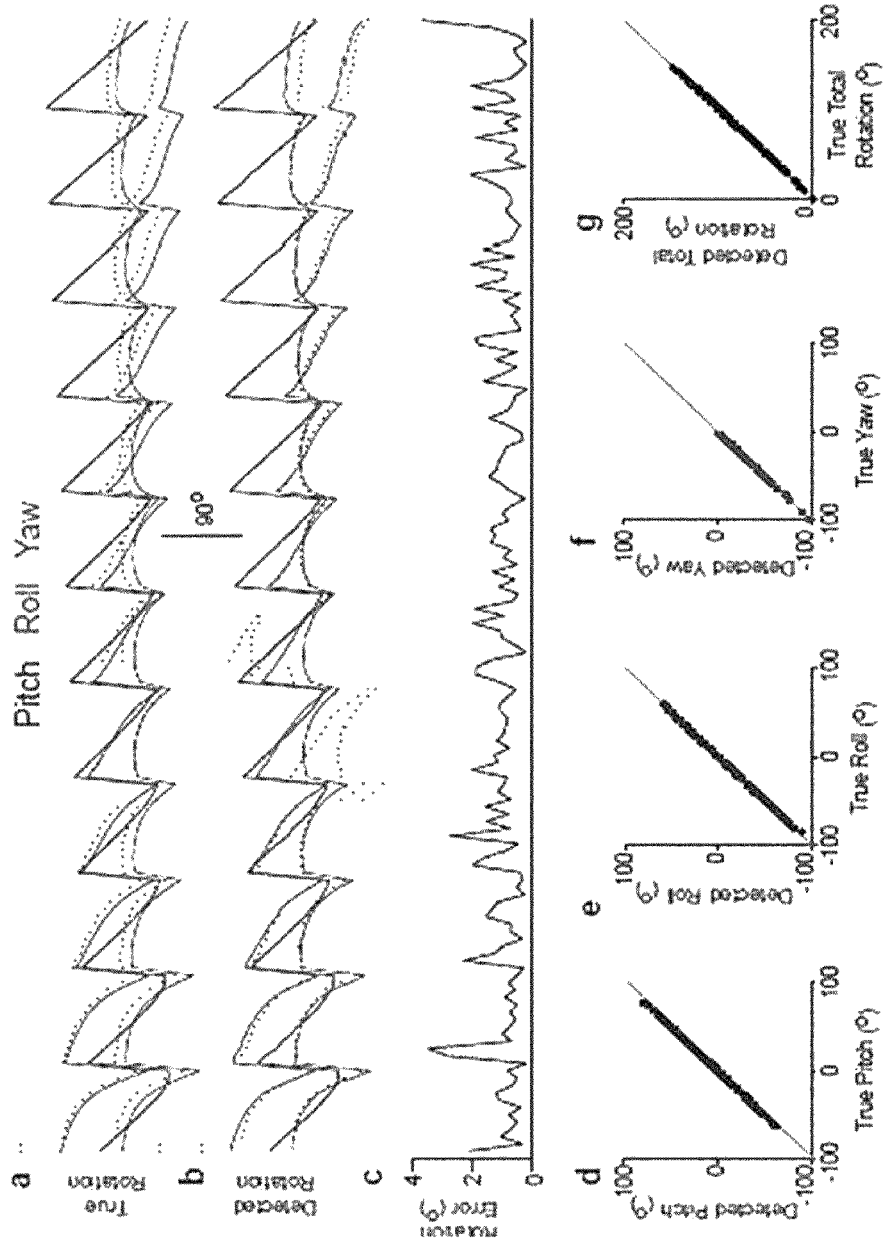
FIG. 14 shows accuracy testing of the head tracking system.

FIG. 14 shows accuracy testing of the head tracking system. a, true values of pitch (blue), roll (green) and yaw (red) for each orientation produced with the rotation stage to test head tracking accuracy, after transformation to the camera coordinates used for head tracking (see Materials and Methods section 'Measurement of head tracking accuracy'). b, values of pitch, roll and yaw detected by the head-tracking system for each orientation produced using the rotation stage for the data shown in a. c, Total rotation error computed by comparing the rotations in a and b (for details of total rotation error calculation, see Materials and Methods section 'Measurement of head tracking accuracy'). d-g, True values of pitch, roll, yaw and total rotation magnitude for each orientation produced with the rotation stage, compared to the values detected by the head-tracking system.

FIG. 15 shows eye movements in freely exploring rats. a, left and right eye images during free movement with individual pupil positions (red dots, ~5000 data points). Dorsal (d) and posterior (po). b, vertical (marker color) and horizontal (x-axis position) kinetics (y-axis) of eye movements during free movement (excerpt from a). Positive and negative vertical movements are denoted (up and down markers). Magnitude represented (marker color). Behavioral periods indicated. c, eye image (upper) showing the pupil margin used for torsional tracking (outlined in orange) and the extracted section (lower image) from upper image including tracked pupil margin (red). d, torsion of right (green) and left (blue) eyes during free movement. Note eyes can both rotate in the same direction (a), opposite directions (b) and combinations thereof.

FIG. 16 shows eye movements are dictated by head movement and position in freely moving animals. a, schematic detailing how pupil elevation and depression (red pupils) can counteract head roll (yellow) compared to a horizon (black dotted). b, comparison of pupil elevation for left (blue) and right (green) eyes in relation to head roll in a freely moving animal (average and s.e., n=4 animals). c, schematic detailing how eye movements in the horizontal plane (red arrowhead) occur during head pitch. d, horizontal pupil position for left (blue) and right (green) eyes in relation to head pitch in a freely moving animal (average and s.e., n=4 animals). e, schematic detailing how ocular torsion (red arrows depict torsion direction) counteracts head pitch (black arrow) compared to horizon (red line). f, ocular torsion for both left (blue) and right (green) eyes in relation to head pitch during free movement (average and S.E., n=4 animals).

FIG. 17 shows asymmetrical eye movements in freely moving rats. a, distributions of the difference between left and right eye positions for a freely moving (blue) and head-restrained (red) rat. Each point represents the right eye position minus the left eye position for a single frame. Histograms shown for x and y axes. Example image pairs (insert) from positions within the distribution (arrows). Conventions for eye images as in FIG. 15a. b, scatter plot of the difference in left and right eye gaze vectors during free movement. c, plot of the difference in left and right eye gaze vectors during free movement for a single continuous 1.7 second data segment including a gap cross.

FIG. 18 shows eye movements in freely moving animals are not consistent with those needed for binocular fusion. a, schematic for defining lines of sight for re-projection. Left, reference visual target (yellow spot), optical axis (black), projections from visual target to eyeball centers (red). Right, relative changes of right (green) and left (blue) eye re-projections (red). b, rendering of jumping arena showing monitors (far left and right stripes), initial animal position (a), initial gaze position (yellow dot for each eye) and subsequent gaze positions of the two eyes (left, green and right, blue lines, end gaze positions over 1.7 s ending with red dot). Same data as FIG. 17c. c, difference between left and right eye positions for the data shown in b (conventions as FIG. 17a).

FIG. 19 shows overhead binocular overlap. a, schematic outlining binocular overlap (red, modified from[1]). b, schematic for data in panels c and d. c, average (green) dependence of horizontal overlap on head pitch (s.e., thin black lines, n=4 animals). d, dependence of horizontal inferior (black) and posterior (blue) overlap on head pitch (s.e. thin black lines, n=4 animals). Head-centric density plots (inserts) showing probability of visual field overlap (pseudo-color) when animal is pitched down ($\leq 10^{th}$ percentile of head pitch angles, insert left) or pitched up ($\geq 90^{th}$ percentile, insert right, 30° ticks on vertical and horizontal axes). Note that average head roll was 18±1° during nose down pitch. Images (upper inserts) show example eye positions for negative and positive head pitch (same as in FIG. 17a). e, head-centric density plot of average overlap of monocular visual fields during free movement for all head positions (conventions as in d, n=4 animals). f, body-centric density plot of the overlapping fields that includes head and eye movements (conventions as in d,e, n=4 animals). See FIG. 11 for body-centric definition.

FIG. 20 shows shapes moving overhead selectively evoke shelter-seeking behavior. a, schematic of side stimulus presentation. b, animal's trajectory before (blue) and after (red) the onset (black circle) of a black moving bar stimulus presented on one of the side monitors. c, schematic showing stimulus presentation above the rat. d, trajectory before and after the onset of an overhead stimulus. Plot conventions as in b. e, average (s.e. bars) time before the rat's next visit underneath the shelter after stimulus presentation on monitors located beside the arena (Side), above the animal (Overhead), without stimulus presentation (No stim.), or after a randomly chosen time within the dataset (Control). f, fraction of time spent underneath the shelter after stimuli presented on monitors beside the arena or overhead and for the same control condition described for e. Statistically significant group differences (p<0.01) in e and f are denoted (stars, n=3 animals).

Below detailed results are outlined, referring, inter alia, to FIGS. 1 to 20.

Fusing left and right eye images into a single view is dependent on precise ocular alignment, which relies on coordinated movements of the two eyes. During movements of the head this alignment is maintained by numerous reflexes. While rodents share with other mammals the key components of eye movement control, the coordination of eye movements in freely moving rodents is unknown. Here we show, using a custom-built miniaturized ocular videography system, that movements of the two eyes in freely moving rats differ fundamentally from the precisely controlled eye movements used by other mammals to maintain continuous binocular fusion. We show that the observed eye movements serve to keep the visual fields of the two eyes continuously overlapping above the animal during free movement, but not continuously aligned. Overhead visual stimuli presented to rats freely exploring an open arena evoked an immediate shelter-seeking behavior, while the same stimuli were ineffective when presented beside the arena. We suggest that eye movements in freely moving rats provide constant overhead surveillance which would be of substantial evolutionary benefit for predator detection by minimizing blind spots.

Eye Movements in Freely Moving Animals

To record eye movements in freely moving rats we developed a miniaturized ocular-videography system that consisted of two lightweight head-mounted cameras (FIG. 1). Pupil positions in the acquired images were tracked using custom written algorithms. To allow analyses of the observed eye movements in the context of the rat's pose and location on the track, we also tracked the position and orientation (pitch, roll and yaw) of the animal's head using a custom-built tracking system.

In freely moving animals, both eyes were highly mobile (FIG. 15a-b), with large horizontal and vertical excursions of the pupil (FIG. 15b). Both eyes moved continuously while the animal was exploring, but movements markedly reduced in amplitude when the animal stopped making large movements of its head. The dynamics of the movements were complex, regularly disconjugate and often asymmetrical. The images also allowed measurement of ocular torsion (rotation around the optical axis). To quantify torsional rotations in freely moving rats we developed a method for tracking the irregular rough edge of the pupil in the videography images (FIG. 15c). Torsional rotations occurred frequently, and reached relatively large amplitudes (20-30°, FIG. 15d). The dynamics of torsional rotations were also complex, and both cycloversion (rotation of both eyes in the same direction) and cyclovergence (rotation of the eyes in opposite directions) were observed (see a and b in FIG. 15d). On average there was a weak correlation between left and right eye torsion angles; however, the range of angles recorded for one eye for any given angle recorded for the other eye was very broad (FIG. 2). In contrast eyes movements in head-restrained rats were conjugate and infrequent even when the animal was running on a spherical treadmill (FIG. 3).

Influence of Head Movements

Numerous sensory inputs and reflexes contribute to the regulation of eye position or gaze direction. Particularly obvious in the current study was the role of the VOR. As previously observed in restrained rats, roll of the head to the right resulted in elevation of the right pupil and declination of the left pupil and vice versa for roll to the left (FIG. 16a, b). For both freely moving and head-restrained animals, these eye positions were maintained for as long as the roll was maintained (FIG. 4,). Pitching of the head nose-up or down resulted in strong convergent and divergent eye movements respectively (FIG. 16c, d), and these positions were also maintained while the pitch angle was maintained (FIG. 4). In addition, pitching of the head also resulted in complementary torsional rotation of the left and right eyes (FIG. 16e, f). To assess the extent to which the VOR controlled the observed eye positions we built a simple predictive model which predicted eye positions based on pitch and roll of the head. The model was able to predict a large proportion of the tracked eye movements for both vertical (78±2% variance reduction, n=3 animals) and horizontal axes (69±3% variance reduction, n=3 animals, FIG. 5). From this we conclude that a large proportion of the eye movements we observed in freely moving animals were VOR driven.

Consequences for Matching Retinal Images

One very obvious feature of the observed eye movements was that the pointing directions of the two eyes often differed substantially. This observation implies that both the fraction of the retinal images in the left and right eyes that are matching and the location on the retina of any matching regions may vary from moment to moment. To begin to quantify this we first measured the difference in pupil positions (right pupil position-left pupil position, FIG. 17a). If this measure was used for animals with conjugate eye movements (human, primate, cat etc.) differences in pupil positions would be minimal, other than during convergence and divergence. In the freely moving rat, the horizontal pupil position differences were both negative (one or both eyes rotating temporally away from the nose) and positive (convergent eye positions). This was also the case for the vertical plane where positive differences represented a vertical divergence with the right eye more dorsal than the left, and vice-versa for negative differences. The range of pupil position differences was large in both planes, with an average standard deviation of almost 20° (FIG. 6). Furthermore, the differences in pupil positions in both planes changed continuously as the animal was moving with the horizontal difference being strongly related to head pitch (FIG. 7). In contrast, in head-restrained animals the differences in pupil positions were minimal (FIG. 17a) with the standard deviation nearly 4 times smaller than that for freely moving animals (FIG. 6). We also confirmed that these differences in pointing direction (gaze vectors) occurred when measured in a 'world coordinate' system (FIG. 17b) see FIG. 8) and the difference changed continuously, with shifts of over 20° occurring several times per second (FIG. 17c).

We next estimated the extent to which the observed eye movements may represent shifts in fixation onto different objects around the track as the animal performed a single cross of the gap. Since rats have no fovea or pronounced retinal specialization, measuring the extent to which fixation was maintained required an alternative reference point for re-projection over time. We therefore identified a time point shortly before the gap crossing when the animal's head position was at median pitch and roll, and then defined a reference visual target on the jumping track in the animal's field of view (see schematic in FIG. 18a). Projection lines from this reference target into the centers of the left and right eye ball were used to define the point on the surface of the eyeball to be used for re-projection as the eye moved. To gauge the extent to which the observed ocular misalignment caused differences in potential visual targets of the two eyes we rendered the environment around the rat, and followed the location where the re-projection lines contacted objects in the rendered environment (FIG. 18b). Over the 1.7 s required for the animal to perform the gap cross, the majority of eye movements were disconjugate, resulting in a broad range of differences in both eye positions (FIG. 18c) and gaze vectors (FIG. 9). The pupil projection points varied widely over the track (FIG. 18b), and there was very little coordination of the two points on single objects or locations. Note that the projections points were precisely aligned on the reference visual target just prior to the jump. We next calculated the physical distance between the left and right eye projection points down the length and across the width of the track (FIG. 9). Within the animal's viewable environment, the distances separating the two projection points ranged from 0 to ~70 cm on the jumping track. While we were not able to predict exactly what part of the visual space the animal was attending to, the constant changes in ocular alignment in both eye axes were not consistent with the animal shifting its gaze onto different objects of interest. We conclude that the coordination of eye movements in rats is not specialized for maintaining a fixed relationship between the eyes.

Maintenance of Binocular Field

The large collection angle of the rat eye)(~200° combined with the lateral position of the eye on the head result in rats having large monocular visual fields, that share a large overlapping area extending in front, above and behind the animal's head (FIG. 19a). To investigate the extent to which eye movements change the size, shape and location of the overlap of the monocular visual fields, we first generated a model of the animal's monocular visual fields based on optical and physiological properties of the rat eye. The width of the overlapping fields at three different locations around the animal's head (FIG. 19b) varied strongly with the pitch of the animal's head (FIGS. 19c and d, FIG. 10). The width of the binocular field directly in front of the animal's nose, which is generally considered the animal's binocular viewing area, ranged from ~40° to ~110° depending on head pitch. Changes in the extent of the visual field overlap measured at the inferior and posterior locations had strong but complementary dependence on head pitch (FIG. 19d), consistent with the location of the binocular field remaining above the animal as the animal pitched its head. In all animals, the eye movements constantly kept the average overlap of the monocular visual fields above the animal's head (FIG. 19e). The effect of pitch on the location of this region was most clear when it was calculated for the top and bottom 10% of head pitch positions (average −42.4±0.1° for pitch down and 30.2±0.2° pitch up, FIG. 19d, inserts). To further characterize this, we next calculated the position of the average binocular visual field relative to the animal's body (see FIG. 11 for schematic). This 'bird's eye view' of the average overlap shows its location after accounting for the changing location of the visual fields caused by pitch and roll of the animal's head (FIG. 19f). In this reference system, the visual field overlap is predominantly located in-front of and above the animal (FIG. 19f), despite an average nose-down head pitch of 25° (range 80° down to 40° up, FIG. 11). These results indicate that one of the key consequences of the eye movements observed in freely moving rats is that the region of overlap of the left and right visual fields is kept continuously above the animal, consistent with the suggestion that a major function of the rat visual system is to provide the animal with comprehensive overhead surveillance for predator detection.

Behavioral Response to Overhead Stimuli

We next tested whether visual stimuli presented above the animal were capable of eliciting behavioral responses. Naïve rats were placed in an open-field arena surrounded on three sides and above by stimulus monitors (FIG. 20a). The only object inside the open field was a shelter under which the animal could hide. Stimuli presented on the monitors beside the area failed to elicit any detectable changes in the animals' behavior (FIG. 20b). In stark contrast, black moving stimuli presented overhead (FIG. 20c) elicited an immediate shelter-seeking behavior from all animals tested (FIG. 20d). The rats ran immediately and directly to the shelter (FIG. 20e, 20 trials from 3 rats for side stimuli, 12 trials from 3 rats for overhead stimuli), and once there remained under the shelter for significantly extended time periods (FIG. 20f, datasets as for FIG. 20e). As these behavioral responses may not necessarily require binocular viewing of the stimulus, one possibility is that the seemingly disconjugate eye movements, by continuously maintaining overlap of the monocular visual fields, help provide comprehensive surveillance of the region overhead by minimizing or eliminating 'blind spots'. However, it has also been shown for freely moving rats that certain aspects of their visual function, such as visual acuity, are enhanced in the binocular field compared to the monocular field, thus it is also possible that these eye movements provide a direct enhancement of their vision by maintaining binocularity overhead. In summary, we conclude that while the observed eye movements preclude the possibility that rats continuously maintain binocular fusion while moving, they provide a benefit to the animal by facilitating comprehensive overhead surveillance as a defense against predation.

Discussion

In primates, eye movements are precisely coordinated to maintain fixation of visual targets[15]. Precise ocular alignment is critical for binocular fusion. For foveal vision in humans misalignment of more than ⅓-1° results in double vision[16]. For peripheral vision fusion is more tolerant to ocular misalignment, however, even there misalignment of more than a few degrees results in diplopia[17], and pupils moving in opposite vertical directions is associated with serious pathology[18]. In freely moving rats the difference in the gaze directions of the left and right eyes, which is a measure of the alignment of the eyes on a single target, has a range of more than 40° horizontally and more than 60° vertically. This range excludes the possibility that primate-like binocular fusion is continuously maintained when the animal is moving. Instead, eye movements in the rat are specialized for continuously maintaining overlap of the monocular visual fields above the animal as the head moves. It is clear from their low acuity[19], lack of fovea[13] and lack of significant capacity for accommodation[20] that rat vision is specialized along different lines to that of fovate mammals, and their strategy for eye movement control appears to be different as well. For the ground dwelling rodent, foraging is actively pursued at dusk, and local changes in the environment are detected using mystacial vibrissa[21] and olfaction[22] both of which are associated with rapid head movements in all planes[23]. For rats, birds of prey such as owls[9] are a major predator, and as vision is the only sense that allows predator detection at a distance, the wide panoramic field of view[1,20], large depth of field[24] and maintenance of comprehensive overhead surveillance based on a system which counteracts the rapid head movements may be of substantial evolutionary advantage.

The eye movements observed here do not imply that rats are completely incapable of binocular fusion, stereoscopic depth perception or detailed vision. Rats can use their vision for depth perception[2,8] and are also capable of quite sophisticated visual object recognition[4]. The variable alignment of the gaze directions of the eyes during head movements do imply, however, that for rats to fuse the two monocular images or have stereoscopic depth perception they must either use a behavioral strategy to align the two monocular images (orient their head in a positions which allows or facilitates fusion), or alternatively have an another mechanism that allows them to identify matching components in the two retinal images. Some non-predatory bird species combine both panoramic vision (predator detection) with stereoscopic vision of close by objects (bill vision) by using multiple retinal specializations[25] and other birds have behavioral strategies involving a combination of head-movements for switching between distinct modes of viewing. Rats may use similar strategies, in which the animal assumes a particular posture bringing both eye images into registration when detailed vision is required. An alternative proposal is that they can fuse left and right images without precise retinal registration by using something like a corollary signal (for review see[26]) to track the eye movements and identify matching retinal locations. This would be somewhat analogous to the mechanism suggested to explain shifting receptive field locations in monkey frontal cortex[26]. However, such a mechanism would require an immense degree of connectivity within the visual areas and there is to date no evidence for this.

In summary, eye movements in freely moving rats are asymmetrical and inconsistent with the animal maintaining continuous fixation of a visual target with both eyes while moving. Instead, the movements keep the animal's binocular visual field above it continuously while it is moving, consistent with a primary focus of the animal's visual system being efficient detection of predators coming from above.

Methods Summary

The miniaturized camera system was secured onto a custom-built headplate which was implanted on the head. The position of the pupil was tracked in each image frame, and the effects of movement of the cameras eliminated by simultaneously tracking anatomical features of the eye (FIG. 12). The accuracy of the pupil detection algorithm was measured to be <1°, and errors associated with tracking the anatomical features estimated to be <<3° (FIG. 13). Head position and orientation were tracked by following the relative position of six infrared-LEDs mounted with the camera system. Tracking accuracy was <1° for all three axes of head orientation (FIG. 14)

FIG. 21 shows a miniaturized ocular-videography system for imaging during free movement according to this invention, requiring continuous tracking of the head and eyes to determine visual input. We developed a 2P-compatible, all-optical system for head and eye tracking in rodents. Head tracking with 6 DOF employed infrared LEDs mounted on the microscope and imaged by multiple overhead cameras, while miniaturized camera systems with specialized, custom-built optics and electronics were used to image the eyes. Calibration procedures based on the Tsai camera model realistically incorporated radial lens distortion, and for custom-built camera systems decentering and thin-prism distortions as well. To detect eye movements, we directly compared 3D geometric models of the eye and pupil to each observed image, minimizing an objective function over eye rotation angles and pupil dilation radii. We found that this approach, which detected the 2D pupil boundary and 3D eye rotation simultaneously in a single step, was more robust than previous methods with an intermediate stage of 2D feature detection, allowing our system to operate effectively at lower contrast. Since the pupil-iris boundary deviated slightly from a perfect circle, with an uneven, crenellated appearance on a fine spatial scale, we also detected ocular torsion by measuring rotation of this rough boundary through 3D space. The eye tracker was self-calibrating in that animals were not required to fixate a presented target, aiding the use of this system in rodents where such training is impossible. Finally, based on the appearance of the eyeball-eyelid boundary we defined anatomically based coordinate axes and baseline pupil positions that were consistent across animals, even when the location and orientation of eye tracking cameras varied. Together, these tracking systems and analysis methods allowed stimulus presentation monitors and other environmental features to be mapped continuously onto each pupil plane, and gaze vectors for each eye to be projected into the animal's environment.

According to FIG. 22 accurately recording eye movements is essential to understanding how an animal moves its eyes to establish vision. Rodents are a commonly used model for the mammalian visual system, but it is not known how they move their eyes during free movement. We describe here a custom-built ocular videography system light enough to be carried on the head of a freely moving rat. Each camera, complete with mounting arm and infrared (IR) illumination weighs 1.8 g. Rats comfortably carry 2 cameras, one recording the movements of each eye. The monochrome camera chips (Aptina) are capable of recording 752×480 pixel images at a maximum frame rate of 60 Hz. Using a 45° IR reflector allows the cameras to be positioned in a way that minimizes disturbance to the animal's visual field. Illumination from an IR LED (850 nm) provides consistent image quality during normal exploratory behaviors and jumping. Image quality and resolution is good enough to identify the fine detail of the edge of the iris, which can be used for the detection of ocular torsion. The camera chip can be controlled with a two-wire serial interface and is able to transmit image data over a twisted pair using low voltage differential signalling (LVDS). To reduce rotational stiffness we have built 2 m long custom cables by twisting enameled 50 μm dia. copper wires. The signals are decoded on a custom built board using a standard LVDS deserializer (12 bit) and an additional two-wire serial bus buffer. These signals are transmitted to a demonstration board (Demo X, Aptina) equipped with an USB interface. The eye-cameras are deployed in combination with a fully optical head-orientation detection system consisting of 6 IR LEDs mounted on the miniature two-photon microscope with the miniaturized cameras, and a set of 4 external overhead cameras. All cameras (especially the eye cameras which have no exposure signal output) are synchronized using an intensity ramp of both, the position as well as the eye illumination LEDs.

All of the features disclosed in the application documents are claimed as being essential to the invention in as far as they are novel over the prior art either individually or in combination with each other.

LIST OF REFERENCES

1 Camera system
11 Camera
2 Head mount
3 Image sensor
4 Decoder
5 Optical axis of camera system 1
6 light emitting element
7 IR-transmission filter
8 Position tracking system
91 Tracking arms
92 Head movement detection device
10 Light emitting elements
11 Lens unit
110 Plano-convex lens
120 Convex lens
12 Processor
13 Core engine
100 Ocular Videography System

The invention claimed is:

1. An ocular videography system for tracking eye movements of an animal comprising:
   a) a camera system suitable for being positioned on a head of an animal to track eye movements of at least one eye of the animal, said camera system comprising at least one image sensor as well as at least one decoder for decoding a signal detected by the image sensor, wherein the at least one decoder is physically separate from the at least one image sensor;
   b) a head mount on which the camera system is fixed or fixable, wherein the camera system is designed in such a way to detect movements of the eye and/or a movement of the head of the animal in a vertical direction, horizontal direction, torsional direction, or combinations thereof, relative to an optical axis of the camera system or the optical axis of the eye of the animal, or both, without interfering with natural motion dynamics of the animal; and
   c) a head position tracking system designed to track a position of the head of the animal within a predefined, stationary coordinate system originating outside of the body of the animal, wherein said head position tracking system comprises three tracking arms mounted on the head mount in a predefined position to each other, wherein each of the tracking arms comprises one or more light emitting elements, and the head position tracking system further comprises a head movement detection device mounted off of the body of the animal and stationary within the coordinate system, wherein the head movement detection device is able to detect movement of the tracking arm light emitting elements and is able to calculate a position of the head of the animal within said stationary coordinate system according to position and/or movement of the tracking arm light emitting elements.

2. The ocular videography system according to claim 1, wherein the camera system is designed and mounted securely on the head mount without interfering with the animal's field of view.

3. The ocular videography system according to claim 1, wherein the decoder for decoding the signal detected by the image sensor is mounted off of the animal.

4. The ocular videography system according to claim 1, wherein the camera system comprises at least one light emitting element for guiding and emitting light towards the eye of the animal, at least one light reflector for reflecting at least partially the light reflected from the eye of the animal to the image sensor of the camera system, wherein the camera system is mounted on the head mount outside of a visual field of the eye of the animal.

5. The ocular videography system according to claim 4, wherein the camera system light emitting element is arranged within the camera system such that it illuminates the eye of the animal off-axis to the optical axis of the eye of the animal.

6. The ocular videography system according to claim 4, wherein the camera system light emitting element is a light emitting diode (LED) emitting light at least in the infrared (IR) optical spectrum, which is outside the animal's visible spectrum.

7. The ocular videography system according to claim 6, wherein the reflector transmits at least partially light in the visible spectrum of the animal and reflects light in the infrared spectrum of light.

8. The ocular videography system according to claim 6, further comprising an IR-transmission filter as an element of the camera system, wherein said IR-transmission filter is arranged in an optical path of the light emitted by the camera system light emitting element and prevents superimposition of light in the visible optical spectrum with the light emitted by said camera system light emitting element.

9. The ocular videography system according to claim 4, wherein the camera system comprises a lens unit for guiding light at least partially emitted by the camera system light emitting element into the image sensor of the camera system.

10. The ocular videography system according to claim 9, wherein the lens unit comprises a plano-convex lens having an aperture between 0.02 mm and 1.2 mm.

11. The ocular videography system according to claim 9, wherein the lens unit is glued to a camera chip.

12. The ocular videography system according to claim 1 further comprising a core engine implemented within a processor of the camera system controlling measurement parameters of the camera system and capable of streaming data onto one or more hard drives.

13. The ocular videography system according to claim 12, wherein the core engine is capable of processing independent eye movements of both eyes of the animal.

14. An ocular videography system for tracking eye movements of an animal comprising:

a) a camera system suitable for being positioned on a head of an animal to track eye movements of at least one eye of the animal, said camera system comprising at least one image sensor as well as at least one decoder for decoding a signal detected by the image sensor, wherein the at least one decoder is physically separate from the at least one image sensor;

b) a head mount on which the camera system is fixed or fixable, wherein the camera system is designed in such a way to detect movements of the eye and/or a movement of the head of the animal in a vertical direction, horizontal direction, torsional direction, or combinations thereof, relative to an optical axis of the camera system or the optical axis of the eye of the animal, or both, without interfering with natural motion dynamics of the animal; and c) a head position tracking system designed to track a position of the head of the animal within a predefined, stationary coordinate system originating outside of the body of the animal, wherein said head position tracking system comprises three tracking arms mounted on the head mount in a predefined position to each other, wherein each of the tracking arms comprises one or more tracking arm light emitting elements, and wherein the camera system comprises at least one camera system light emitting element for guiding and emitting light towards the eye of the animal, at least one light reflector for reflecting at least partially the light reflected from the eye of the animal to the image sensor of the camera system, wherein the camera system is mounted on the head mount outside of a visual field of the eye of the animal, and wherein the system is able to calculate a position of the head or eye of the animal within a stationary coordinate system according to position and/or movement of light received from the reflector and/or tracking arm light emitting elements.

15. The ocular videography system according to claim 14, wherein the decoder for decoding the signal detected by the image sensor is mounted off of the animal.

16. The ocular videography system according to claim 14, wherein the camera system light emitting element is arranged within the camera system such that it illuminates the eye of the animal off-axis to the optical axis of the eye of the animal.

17. The ocular videography system according to claim 14, wherein the camera system light emitting element is a light emitting diode (LED) emitting light at least in the infrared (IR) optical spectrum which is outside the animal's visible spectrum.

18. The ocular videography system according to claim 17, further comprising an IR-transmission filter as an element of the camera system, wherein said IR-transmission filter is arranged in an optical path of the light emitted by the camera system light emitting element and prevents superimposition of light in the visible optical spectrum with the light emitted by said camera system light emitting element.

19. The ocular videography system according to claim 14, wherein the camera system comprises a lens unit for guiding light at least partially emitted by the camera system light emitting element into the image sensor of the camera system, wherein the lens unit comprises a plano-convex lens having an aperture between 0.02 mm and 1.2 mm.

20. The ocular videography system according to claim 14 further comprising a core engine implemented within a processor of the camera system controlling measurement parameters of the camera system and capable of streaming data onto one or more hard drives.

* * * * *